(12) United States Patent
Maurer et al.

(10) Patent No.: US 7,094,423 B1
(45) Date of Patent: Aug. 22, 2006

(54) METHODS FOR PREPARATION OF LIPID-ENCAPSULATED THERAPEUTIC AGENTS

(75) Inventors: Norbert Maurer, Vancouver (CA); Kim F Wong, Vancouver (CA); Pieter R. Cullis, Vancouver (CA)

(73) Assignee: INEX Pharmaceuticals Corp., Burnaby (CA)

( * ) Notice: Subject to any disclaimer, the term of this patent is extended or adjusted under 35 U.S.C. 154(b) by 385 days.

(21) Appl. No.: 10/019,199

(22) PCT Filed: Jul. 14, 2000

(86) PCT No.: PCT/CA00/00843

§ 371 (c)(1),
(2), (4) Date: Dec. 20, 2001

(87) PCT Pub. No.: WO01/05374

PCT Pub. Date: Jan. 25, 2001

Related U.S. Application Data

(60) Provisional application No. 60/143,978, filed on Jul. 15, 1999.

(51) Int. Cl.
*A61K 9/127* (2006.01)

(52) U.S. Cl. .................................... 424/450
(58) Field of Classification Search ............... 424/450; 264/4.1, 4.3, 4.6
See application file for complete search history.

(56) References Cited

U.S. PATENT DOCUMENTS

| | | | |
|---|---|---|---|
| 5,262,168 A | * | 11/1993 | Lenk |
| 5,785,992 A | | 7/1998 | Ansell et al. |
| 5,976,567 A | * | 11/1999 | Wheeler |
| 6,365,179 B1 | * | 4/2002 | Zalipsky |
| 6,447,800 B1 | * | 9/2002 | Hope |

FOREIGN PATENT DOCUMENTS

| | | |
|---|---|---|
| WO | WO 98/51278 | 11/1998 |
| WO | WO 99/18933 A2 | 4/1999 |
| WO | WO 99/18933 A3 | 4/1999 |

OTHER PUBLICATIONS

Malone et al PNAS 86, pp 6077-6081, Aug. 1989.*
Schubert Chemistry and Physics of Lipids 58, pp 121-129, 1991.*
Lasic, D. D., "The mechanism of vesicle formation", *Biochem. J.* 1988, vol. 256, pp 1-11.
Lasic, D. D., "The Spontaneous Formation of Unilamellar Vesicles", *Journal of Colloid and Interface Science, 1988* vol. 124, No. 2, pp 428-435.

* cited by examiner

*Primary Examiner*—Gollamudi S. Kishore
(74) *Attorney, Agent, or Firm*—Marina Larson & Associates, LLC

(57) ABSTRACT

Fully lipid-encapsulated therapeutic agent particles of a charged therapeutic agent are prepared by combining a lipid composition containing preformed lipid vesicles, a charged therapeutic agent, and a destabilizing agent to form a mixture of preformed vesicles and therapeutic agent in a destabilizing solvent. The destabilizing solvent is effective to destabilize the membrane of the preformed lipid vesicles without disrupting the vesicles. The resulting mixture is incubated for a period of time sufficient to allow the encapsulation of the therapeutic agent within the preformed lipid vesicles. The destabilizing agent is then removed to yield fully lipid-encapsulated therapeutic agent particles. The preformed lipid vesicles comprise a charged lipid which has a charge which is opposite to the charge of the charged therapeutic agent and a modified lipid having a steric barrier moiety for control of aggregation.

20 Claims, 5 Drawing Sheets

US 7,094,423 B1

METHODS FOR PREPARATION OF LIPID-ENCAPSULATED THERAPEUTIC AGENTS

This application claims the benefit of Provisional Application No. 60/143,978, filed Jul. 16, 1999.

FIELD OF THE INVENTION

This invention relates to a novel method for making particles of lipid-encapsulated therapeutic agents, and in particular, lipid-encapsulated therapeutic nucleic acid particles which may be useful in antisense therapy or gene therapy.

BACKGROUND OF THE INVENTION

The concept of using lipid particles as carriers for therapeutic agents has been considered by numerous people. Formulations have relied on complexation of therapeutic agent to the outside of the lipid particle, or actual entrapment of the therapeutic agent, although the ability to make formulations of either type depends on a matching of the characteristics of the lipids and the therapeutic agent, as well as the methods employed to make the particle. In the case of particles with entrapped therapeutic agents, the entrapment method may be passive, i.e., the lipid particles are assembled in the presence of the therapeutic agent, some of which happens to get trapped; or active, i.e, the therapeutic agent is drawn or forced into the interior of a lipid particle as a result of an induced gradient of some type. Notwithstanding the many efforts to utilize lipid particles as carriers, there remain problems which may limit actual applications of lipid-entrapped therapeutic agents. These include low levels of therapeutic agent incorporation on a drug/lipid basis, low efficiency's of capture of the therapeutic agent, and lack of a suitable procedure for larger scale manufacturing of the lipid-encapsulated therapeutic agent particles.

Large scale manufacturing of fully lipid-encapsulated therapeutic agent particles has not been achieved where there is a significant electrostatic interaction between the lipid and the therapeutic agent. A basic problem is aggregation. Aggregation normally results when charged lipid is mixed with oppositely charged therapeutic agent, resulting in a solution containing a milky flocculent mass which is not useable for further processing, let alone for therapeutic use. The aggregation problem has prevented the development of therapeutic compositions which could be of great utility.

Bench scale formulations using charged lipid and oppositely charged therapeutic agent have been successfully achieved using cationic lipids and anionic nucleic acids in a passive encapsulation process described in U.S. Pat. No. 5,705,385 to Bally et al. (PCT Applic. No. WO 96/40964; See also U.S. patent application Ser. Nos. 08/484,282; 08/485,458; 08/660,025; and 09/140,476) and PCT patent Applic. No. WO 98/51278 to Semple et al. (See also U.S. patent application Ser. No. 08/856,374) all assigned to an assignee of the instant invention and incorporated herein by reference. See also Wheeler et al. (1999) Stabilized plasmid-lipid particles: Construction and characterization. Gen. Ther. 6:271–281. These techniques employ an aggregation preventing lipid, such as a PEG-lipid or ATTA-lipid (disclosed in co-pending U.S. patent application Ser. No. 08/996,783 which is incorporated herein by reference), which effectively prevents complex aggregate formation. Resulting fully lipid-encapsulated therapeutic agent particles have excellent pharmaceutical characteristics, such as controlled size (in the 30–250 nm range), full encapsulation (as measured by nuclease resistance, for example) and stability in serum.

WO98/51278 describes a bench scale procedure for the preparation of the lipid-encapsulated therapeutic agent particles using passive entrapment. This known method employs the two basic steps of lipid hydration and liposome sizing. In the lipid hydration step, a cationic lipid solution (95% EtOH solvent) is added dropwise into an agitated reservoir containing polynucleotide therapeutic agent in citrate buffer (pH 3.8) to a final composition of 40% EtOH, 9.9 mg/ml lipid and 2.0 mg/ml polynucleotide. Lipid particles resulting from this hydration step are typically 400 nm diameter and greater, which is too large for general use as a therapeutic. Because of this, extensive post-formulation processing such as high temperature extrusion (at 65° C.) and optionally freeze-thawing (from liquid nitrogen to 65° C. waterbath) is required to obtain suitably-sized lipid particles. The efficiency of encapsulation using this is fairly high (60–90%) in terms of recovered final drug:lipid ratio, but the absolute efficiency of incorporation of starting polynucleotide into the final particle formulation is sub-optimal (25–45%).

Commercial large scale manufacturing of these particles is not efficiently achieved using traditional methods employed in the liposome field. These problems exist notwithstanding the great deal of art on the manufacturing of liposome/drug formulations that has emerged since the first description of liposome preparation by Bangham, AD. et al. (1965) "The action of steroids and streptolysin S on the permeability of phospholipid structures to cations", J. Mol. Biol. 13, 138–147.

Known large scale manufacturing techniques for lipid particles can be broadly classified into the following categories: 1) Lipid Film Hydration (i.e. Passive entrapment); 2) Reverse Phase Evaporation; 3) High-Pressure extrusion; 4) and Solvent injection (dilution) (see for example U.S. Pat. Nos. 4,752,425 and 4,737,323 to Martin et al). Particular instruments for lipid particle manufacturing disclosed in the art include: U.S. Pat. Nos. 5,270,053 and 5,466,468 to Schneider et al; Isele, U. et al. (1994) Large-Scale Production of Liposomes Containing Monomeric Zinc Phthalocyanine by Controlled Dilution of Organic Solvents. J. Pharma. Sci. vol 83 (11) 1608–1616; Kriftner, R W. (1992) Liposome Production: The Ethanol Injection Technique, in Bruan-Falco et al., eds, Liposome Derivatives, Berlin, Springer-Verlag, 1992, pp. 91–100; Kremer et al. (1977) Vesicles of Variable Diameter Prepared by a Modified Injection Method. Biochemistry 16 (17): 3932–3935; Batzri, S. and Korn, ED. (1973) Single Bilayer Liposomes Prepared Without Sonication, Bioch. Biophys. Acta 298: 1015–1019.

None of the above noted methods or instruments are suitable for scale up of formulations of charged lipid and oppositely charged therapeutic agents with the excellent pharmaceutical characteristics of Bally et al., supra, and Semple et al., supra. The manufacturing techniques set out in Bally et al., supra, and Semple et al., supra were developed only for 1–100 ml preparations, and are cumbersome and lead to unsustainable inefficiencies in large scale manufacturing (i.e. at the scale of 20–200 liters).

The instant invention provides, for the first time, methods for the large-scale preparation of fully encapsulated lipid-therapeutic agent particles where the lipid and therapeutic agent are oppositely charged. These particles are useful as therapeutic compositions and for experimentation and otherwise. It is an object of this invention to provide such methods.

SUMMARY OF THE INVENTION

In accordance with the present invention, fully lipid-encapsulated therapeutic agent particles of a charged therapeutic agent are prepared by combining a lipid composition comprising preformed lipid vesicles, a charged therapeutic agent, and a destabilizing agent to form a mixture of preformed vesicles and therapeutic agent in a destabilizing solvent. The destabilizing solvent is effective to destabilize the membrane of the preformed lipid vesicles without disrupting the vesicles. The resulting mixture is incubated for a period of time sufficient to allow the encapsulation of the therapeutic agent within the preformed lipid vesicles. The destabilizing agent is then removed to yield fully lipid-encapsulated therapeutic agent particles. The preformed lipid vesicles comprise a charged lipid which has a charge which is opposite to the charge of the charged therapeutic agent and a modified lipid having a steric barrier moiety for control of aggregation. The modified lipid is present in the preformed vesicles in an amount effective to retard, but not prevent, aggregation of the preformed vesicles. In a preferred embodiment of the invention, effective to provide efficient formation of lipid particles on large scale (for example 20–200 liters), a therapeutic agent solution comprising nucleic acids (for example antisense oligodeoxynucleotides) is combined with preformed lipid vesicles in a 25–40% solution of aqueous ethanol. Incubation of this mixture of a period of about 1 hour is sufficient to result in the spontaneous production of fully encapsulated therapeutic agent particles.

DETAILED DESCRIPTION OF THE INVENTION

Definitions

Figure 1:
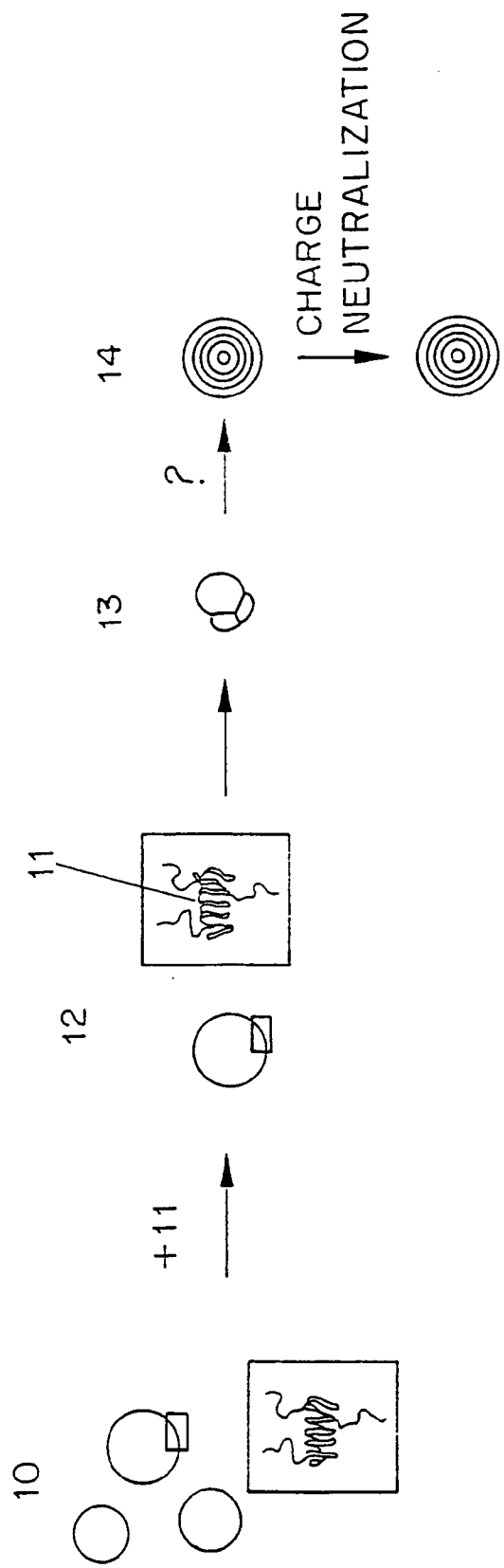
FIG. 1 shows a possible model of the mechanistic steps of the method of the invention.

While the terms used in the application are intended to be interpreted with the ordinary meaning as understood by persons skilled in the art, some terms are expressly defined to avoid any ambiguity. Thus, as used in the specification and claims of this application the term:

charged lipid refers to a lipid species having either a cationic charge or negative charge or which is a zwitterion which is not net neutrally charged, and generally requires reference to the pH of the solution in which the lipid is found.

destabilization refers to modification of the properties of a lipid membrane as a result of interaction with a solvent. When the membrane is destabilized, the fundamental morphology of the original lipid membrane is preserved. However, the leakage rate of low molecular weight solutes increases and lipids can "flip-flop" across the membrane and exchange rapidly with other lipid particles. Destabilization of a lipid membrane is observed in the invention, for example, at ethanol concentrations of 25–40%. Solvents which achieve destabilization but not disruption of lipid vesicles are referred to herein as destabilizing solvents.

disruption refers to modification of the properties of a lipid membrane such that the fundamental morphology of the original membrane is lost. Disruption of a lipid membrane is observed, for example, at ethanol concentrations of >60%.

fully encapsulated refers to lipid particles in which the therapeutic agent is contained in the lumen of a lipid vesicle such as a liposome, or embedded within a bilayer of a lipid particle such that no part of the therapeutic agent is directly accessible to the external medium surrounding the lipid particle. Lipid particles in which the therapeutic agent is fully encapsulated are distinct from particles in which a therapeutic agent is complexed (for example by ionic interaction) with the exterior of the particle, or from particles in which the therapeutic agent is partially embedded in the lipid and partially exposed to the exterior medium. The degree of encapsulation can be determined using methods which degrade available therapeutic agent. In the case of a polynucleotide, these methods include S1 Nuclease Digestion, Serum Nuclease, and Micrococcal Nuclease analysis. Alternatively, an OliGreen™ assay can be employed. In a quantitative sense, a "fully encapsulated" therapeutic agent is one where less than 10% of the therapeutic agent, and preferably less than 5% of the therapeutic agent in a lipid particle is degraded under conditions where greater than 90% of therapeutic agent is degraded in the free form. It should further be noted that additional therapeutic agent(s) may be associated with the lipid particle by complexation or another manner which is not fully encapsulated without departing from the present invention.

hydration refers to a common process by which lipid particles, including liposomes, are formed. In this process, the amount of water in the solvent surrounding the lipids is increased from a concentration of around 5% or less (at which concentration the lipid molecules are generally individually solvated) to a concentration of 40–60% or greater (at which lipids spontaneously form into membranes, micelles or particles).

lipid refers to a group of organic compounds that are esters of fatty acids and are characterized by being insoluble in water but soluble in many organic solvents. They are usually divided in at least three classes: (1) "simple lipids" which include fats and oils as well as waxes; (2) "compound lipids" which include phospholipids and glycolipids; and (3) "derived lipids" such as steroids. A wide variety of lipids may be used with the invention, some of which are described below.

preformed vesicle refers to the starting lipid composition used in the method of the invention which contains lipid vesicles. These vesicles have a self-closed structure of generally spherical or oval shape formed from one or more lipid layers and having an interior lumen containing a part of the solvent. The vesicles may be unilamellar, oligolamellar or multilamellar structures.

The invention disclosed herein relates to a novel method for making lipid-encapsulated therapeutic agent particles which is particularly applicable to the large-scale manufacture of such particles when the lipid and therapeutic agent are oppositely charged, such as found in formulations of cationic lipid and anionic polynucleotides. This invention relies upon the surprising and unexpected observation that combining preformed lipid vesicles with a solution of therapeutic agent can result spontaneously in the formation of particles of fully lipid-encapsulated therapeutic agent of a therapeutically useful size. Thus, fully lipid-encapsulated therapeutic agent particles are formed in accordance with the invention by a method comprising the step of combining a lipid component comprising preformed lipid vesicles and a solution of the therapeutic agent and incubating the resulting mixture for a period of time to result in the encapsulation of the therapeutic agent in the lipid vesicles. The lipid component further comprises a solvent system which is effective to destabilize the membrane of the lipid vesicles without disrupting the vesicles.

The method of the invention has several important characteristics which make it of substantial utility to the art. First, it is a large-scale method which can be used to make substantial quantities (e.g. >100 g) of the encapsulated therapeutic agent in a single batch. Second, the size of the preformed lipid vesicles is substantially maintained, such that processing of the lipid particles after introduction of the therapeutic agent to obtain particles of therapeutically useful size is not necessary. Third, the efficiency of encapsulation is high. Fourth, the amount of therapeutic agent loaded into the particles is high.

The lipid particles used in the present invention are formed from a combination of several types of lipids, including at least (1) a charged lipid, having a net charge which is opposite to the charge of the therapeutic agent; and (2) a modified lipid including a modification such as a polyethylene glycol substituent effective to limit aggregation. In addition, the formulation may contain a neutral lipid or sterol. In formulating the lipid particles using all of the above-mentioned components, the following amounts of each lipid components are suitably used: 10 to 40 mol % charged lipid; 25 to 45 mol % neutral lipid, 35–55 mol % sterol; and 0.5 to 15 mol % modified lipid. Specific lipid components may be selected from among the following non-limiting examples.

Charged Lipids

A wide variety of charged lipids and oppositely charged therapeutic agents may be used with the invention. Examples of such compounds are available and known to persons skilled in the art. The following lists are intended to provide illustrative, non-limiting examples.

Cationic charged lipids at physiological pH include, but are not limited to, N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP"); 3β-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, Lipofectin™ (commercially available cationic liposomes comprising DOTMA and 1,2-dioleoyl-sn-3-phosphoethanolamine ("DOPE"), from GIBCO/BRL, Grand Island, N.Y., USA); Lipofectamine™ (commercially available cationic liposomes comprising N-(1-(2,3-dioleyloxy)propyl)-N-(2-(sperminecarboxamido)ethyl)-N,N-dimethylammonium trifluoroacetate ("DOSPA") and DOPE from GIBCO/BRL); and Transfectam™ (commercially available cationic lipids comprising dioctadecylamidoglycyl carboxyspermine ("DOGS") in ethanol from Promega Corp., Madison, Wis., USA).

Some cationic charged lipids are titrateable, that is to say they have a pKa at or near physiological pH, with the significant consequence for this invention that they are strongly cationic in mild acid conditions and weakly (or not) cationic at physiological pH. Such cationic charged lipids include, but are not limited to, N-(2,3-dioleyloxy)propyl)-N,N-dimethylammonium chloride ("DODMA") and 1,2-Dioleoyl-3-dimethylammonium-propane ("DODAP").

Anionic charged lipids at physiological pH include, but are not limited to, phosphatidyl inositol, phosphatidyl serine, phosphatidyl glycerol, phosphatidic acid, diphosphatidyl glycerol, poly(ethylene glycol)-phosphatidyl ethanolamine, dimyristoylphosphatidyl glycerol, dioleoylphosphatidyl glycerol, dilauryloylphosphatidyl glycerol, dipalmitoylphosphatidyl glycerol, distearyloylphosphatidyl glycerol, dimyristoyl phosphatic acid, dipalmitoyl phosphatic acid, dimyristoyl phosphatidyl serine, dipalmitoyl phosphatidyl serine, brain phosphatidyl serine, and the like.

Some anionic charged lipids may be titrateable, that is to say they would have a pKa at or near physiological pH, with the significant consequence for this invention that they are strongly anionic in mild base conditions and weakly (or not) anionic at physiological pH. Such anionic charged lipids can be identified by one skilled in the art based on the principles disclosed herein.

Neutral Lipids and Sterols

The term "neutral lipid" refers to any of a number of lipid species which exist either in an uncharged or neutral zwitterionic form a physiological pH. Such lipids include, for example, diacylphosphatidylcholine, diacylphosphatidylethanolamine, ceramide, sphingomyelin, cephalin, cholesterol, cerebrosides and diacylglycerols.

Modified Lipids

Certain preferred formulations used in the invention include aggregation preventing lipids such as PEG-lipids or polyamide oligomer-lipids (such as an ATTA-lipid), and other steric-barrier or "stealth"-lipids. Such lipids are described in U.S. Pat. No. 4,320,121 to Sears, U.S. Pat. No. 5,820,873 to Choi et al., U.S. Pat. No. 5,885,613 to Holland et al., WO 98/51278 (inventors Semple et al.), and U.S. patent application Ser. No. 09/218,988 relating to polyamide oligomers, all incorporated herein by reference. These lipids prevent precipitation and aggregation of formulations containing oppositely charged lipids and therapeutic agents. These lipids may also be employed to improve circulation lifetime in vivo (see Klibanov et al. (1990) FEBS Letters, 268 (1): 235–237), or they may be selected to rapidly exchange out of the formulation in vivo (see U.S. Pat. No. 5,885,613). Particularly useful exchangeable lipids are PEG-ceramides having shorter acyl chains (i.e, C14 or C18, referred to herein as PEG-CerC14 and PEG-CerC18) or PEG-PE having a C14 acyl chain.

Some lipid particle formulations may employ targeting moieties designed to encourage localization of liposomes at certain target cells or target tissues. Targeting moieties may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, all incorporated herein by reference) and other features useful for in vivo and/or intracellular delivery.

The preformed lipid vesicles may be prepared in a solution of ethanol or other organic solvent using a simple lipid hydration step. The percentage of ethanol or other organic solvent must be selected such that the lipid particles do not disassemble or redissolve into the solvent (generally at >60% ethanol) but provide conditions which permit the spontaneous encapsulation process of the invention (approx. 5%–50% ethanol, more preferably 25–40% ethanol). Alternatively, additional components such as detergents may be included in the lipid vesicle solution which contribute to the destabilization of the membrane. For purpose of this specification, "organic solvent" means either a completely organic solvent (i.e. 100% ethanol) or a partially organic solvent (such as ethanol in water, ie. 20% ethanol, 40% ethanol, etc.). A wide variety of water miscible organic solvents may be used including ethanol or other alcohols, acetonitrile, dimethylformamide, DMSO, acetone, other ketones, and the like. Solvents with greater or lesser polarity may be useful in some cases. Detergent solutions include β-D-glucopyranoside, Tween 20 and those set out in WO 96/40964 and U.S. patent application Ser. No. 09/169,573, both incorporated herein by reference, and any other detergent or steric barrier compound that can provide the same solubility features, and/or can prevent particle aggregation during mixing of oppositely charged lipid and therapeutic agent. Preferably all organic solvents or detergent solutions are pharmaceutically acceptable in trace amounts, or greater, in order that the formulation process does not preclude patient administration.

Anionic therapeutic agents include any therapeutic agent with a net negative charge, or having a negatively charged group that is able to interact with a cationic lipid without being blocked by other cationic charge groups of the therapeutic agent. Such therapeutic agents include any known or potential therapeutic agent, including all drugs and compounds such as, but not limited to, oligonucleotides, nucleic acids, modified nucleic acids (including protein-nucleic acids and the like), proteins and peptides with negative charge groups, conventional drugs such as plant alkaloids and analogues having negative charge groups, and the like. Therapeutic agents which are not inherently anionic may be derivatized with anionic groups to facilitate their use in the invention. For example, paclitaxel can be derivatized with a polyglutamic acid group linked to the 2' carbon.

Cationic therapeutic agents include any therapeutic agent with a net positive charge, or having a positively charged group that is able to interact with a negative lipid without being blocked by other negative charge groups of the therapeutic agent. Such therapeutic agents include any known or potential therapeutic agent, including all drugs and compounds such as, but not limited to modified nucleic acids linked to cationic charges, proteins and peptides with positive charge groups, conventional drugs such as plant alkaloids and analogues having positive charge groups, and the like. Therapeutic agents which are not inherently cationic may be derivatized with cationic groups to facilitate their use in the invention.

Typically, charged therapeutic agents are initially provided in buffered aqueous solution, generally containing some amount of ethanol or other organic solvent. Salt concentration can strongly effect the self assembly process (see U.S. patent application Ser. No. 09/169,573 incorporated herein by reference) employed in the invention, so the buffered salts employed need to be carefully selected. Further, all buffers must be pharmaceutically acceptable, as traces may remain in the final formulation. A suitable buffer is 300 mM citrate buffer for phosphorothioate oligodeoxynucleotides. For phosphodiester-based oligodeoxynucleotides and plasmid DNA which have lower binding affinities, a buffer of lower ionic strength is appropriate. For example, typical citarte concentrations are between 25 and 150 mM, with maximum entrapment occurring at around 50 mM. The amount of ethanol or other organic solvent which may be included is controlled by the solubility of the therapeutic agent in the aqueous organic mixture, and also by the desired characteristics of the final mixture of therapeutic agent and preformed lipid vesicles.

The selection of lipids, destabilizing solvent and therapeutic agents are made to work in concert to provide fully lipid-encapsulated compositions. Thus, if the therapeutic agent is a polyanionic oligonucleotide, the lipid components should be selected to include lipids which are cationic under conditions in the stabilizing solvent. Conversely, if the therapeutic agent is cationic, the lipids components should be selected to include lipids which are anionic under the conditions in the destabilizing solvent. This does not mean that all of the lipids included in the lipid solution must be charged, nor does it exclude the incorporation of some quantity of like-charged lipids or of zwiterrionic lipids. It merely means that the lipid solution should include lipids which have a net charge which is opposite to the net charge of the therapeutic agent.

The method of the invention employs relatively dilute solutions of lipid particles and therapeutic agent. In general, the therapeutic agent solution will have a concentration of 1 to 1000 mg/ml, preferably 10–50 mg/ml of the therapeutic agent, to yield a final concentration (after mixing with the preformed lipid vesicles) in the range of 0.2–10 mg/ml, preferably about 1–2 mg/ml. Preformed lipid vesicles are combined with the therapeutic agent solution such that the resulting lipid concentration (after mixing with therapeutic agent solution) is about 1.5–30 mg/ml (about 2–40 mM), preferably 10 mg/ml. A preferred composition for preformed vesicles for use with polynucleotide therapeutic agent is made at the standard lipid ratios (PEG-cerC14: DODAP: DSPC:Chol (molar ratios 5:25:25:45). This solution, in 100% ethanol, is diluted to 5–50% ethanol, preferably 40% ethanol by mixing with aqueous buffer, for example 300 mM citrate, pH 4.0.

Encapsulation results upon stirring the lipid solution and the oligonucleotide solution together until well mixed, and then incubating with no mixing or gentle mixing for a period of from about 1 to 2 hours. The resulting solution is then dialyzed to remove ethanol or other material which destabilizes the lipid particle membrane. pH adjustments may be used to neutralize surface charges (in the case that the charged lipid is titratable) in order to release therapeutic agent which may be complexed with the exterior of the particle.

At the end of the incubation, the method of the invention results in spontaneously-formed fully-encapsulated therapeutic agents particles having a size which is acceptable for therapeutic use and which can be predicted based on the starting side of the preformed lipid vesicles. Thus, in general, a sizing step of the type known in the art is not necessary after the addition of the therapeutic agent. This is advantageous because there is no requirement for application of mechanical stress to the lipid vesicles after incorporation of the therapeutic agent, and thus no risk of loss of or damage to the therapeutic agent. Should further sizing of the product particles be desired, however, an optional step for sizing of the resulting lipid particles may be employed. Further, a sizing step may be employed as part of the preparation of the preformed vesicles prior to the introduction of the therapeutic agent in order to obtain starting vesicles of the desired size.

There are several methods for the sizing of lipid particles, and any of these methods may generally be employed when sizing is used as part of the invention. The extrusion method is a preferred method of liposome sizing. see Hope, M J et al. Reduction of Liposome Size and Preparation of Unilamellar Vesicles by Extrusion Techniques. In: *Liposome Technology* (G. Gregoriadis, Ed.) Vol. 1. p 123 (1993). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for reducing the size of a population of liposomes ("sizing liposomes"). One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in diameter. Homogenization is another method; it relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, Ann. Rev. Biophys. Bioeng., 10:421–450 (1981), incorporated herein by reference. Average liposome diameter may be reduced by sonication of formed liposomes. Intermittent sonication cycles may be alternated with QELS assessment to guide efficient liposome synthesis.

Preferred sizes for liposomes made by the various liposome sizing methods will depend to some extent on the application for which the liposome is being made, but will in general fall within the range of 25 to 250 nm. Specific examples of suitable sizes are set out in the Examples below.

In studying the lipid particles made in accordance with the invention, it was surprisingly found that large empty unilamellar vesicles (LUV), were converted into multilamellar vesicles with entrapped therapeutic agent. While not intending to be bound by any particular mechanism, it is believed that the process which is occurring is as shown in FIG. 1, where a cationic charged lipid and an anionic therapeutic agent are assumed. The process starts with a unilamellar vesicle 10 which as a result of the inclusion of cationic lipids has positive surface charges on the inside and outside surfaces of the bilayer wall. Addition of anionic therapeutic agent, such as antisense oligodeoxynucleotides 11 results in the formation of an intermediate complex 12 in which the therapeutic agent molecules 11 are bound by an ionic/electrostatic mechanism to the oppositely charged lipids on the surface of the LUV.

The next step in the process appears to be an aggregation step, in which aggregates 13 of the LUV/therapeutic agent complexes are formed. This aggregation step is very complex and is apparently dependent on the amount of destabilizing agent (for example ethanol) and the amount of modified lipid in the preformed vesicles, as well as being mediated by the charged therapeutic agent. Some limited knowledge is provided in the art about these processes, but they neither predict nor explain the phenomenon which is the basis of the present invention. It is known that cationic liposome/DNA complexes exhibit a large variety of different structures including clusters of aggregated liposomes with flat double-bilayer diaphragms in the areas of contact, liposomes coated with DNA and (aggregated) multilamellar structures, where DNA is sandwiched between lipid bilayers (Gustafsson et al., 1995; Lasic, 1997; Lasic et al., 1997; Huebner et al., 1999; Xu et al., 1999). The latter structures can be flat stacks of bilayers or liposomes, which frequently exhibit open bilayer segments on their outer surface. Similar structures have been observed following binding of $Ca^{2+}$ to negatively charged liposomes (Papahadjopoulos, 1975; Miller and Dahl, 1982; Rand et al., 1985; Kachar et al., 1986). The structural transformations occurring in these systems were attributed to adhesion-mediated processes such as bilayer rupture and fusion (Rand et al., 1985; Kachar et al., 1986; Huebner et al., 1999). First, liposomes aggregate crosslinked by DNA or $Ca^{2+}$. Rapid spreading of the contact area deforms the liposomes as they flatten against each other. This places the bilayer under increased tension. If the tension (adhesion energy) is high enough, the stress imposed on the lipid membrane can be relieved either by fusion (increase in area/volume ratio) and/or rupture (volume loss). Most bilayers rupture when the area is increased by about 3% (Evans and Parsegian, 1983). Upon bilayer rupture, vesicles collapse flattening against each other to form multilamellar stacks. Membrane-destabilizing agents such as ethanol can modulate the structural rearrangements occurring upon interaction of cationic liposomes with DNA or oligonucleotides.

In the method of the present invention, the formation of multilamellar liposomes from unilamellar vesicles in the presence of ethanol also points to an adhesion-mediated process for their formation. However, the process differs in some way from the complexes with their terminated membranes, since the product in this case is concentric bilayer shells. While ethanol or a comparable destabilizing agent is required for the latter structures to form it is not clear how it affects these structural rearrangements. These rearrangements correlate with the loss of the membrane permeability barrier fr smaller moeclues and rapid lipid exchange, as well as lipid flip-flop (which correlates with alcohol concentration). In addition, the exchange out of the modified lipid from the LUV may be a significant factor in to reorganization of the lipid vesicles. In any event, by some mechanism, the aggregates 13 rearrange to form multilamellar vesicles 14 with the therapeutic agent entrapped between the lamellae and on the inside of the vesicle. This rearrangement is dependent not only on the nature of the aggregates formed, but also on the temperature at which the aggregates are incubated. Some of the therapeutic agent may also remain associated with charges on the exterior of the multilamellar vesicle, and, these may be removed by charge neutralization (for example with acid or base in the case of a titratable charged lipid), or by ion exchange.

Several characteristics of the lipid vesicles and the destabilizing solvent were found experimentally to be of importance to the characteristics of the final products, and the selection of these characteristics can be used to control the characteristics of the product multilamellar vesicles. These characteristics include:

(1) the inclusion of a charged lipid in the preformed lipid vesicles with a charge opposite that of the therapeutic agent;
(2) the inclusion of a modified lipid in an amount sufficient to retard aggregation, but not enough to prevent aggregation. In the case of PEG-CerC$_{14}$, this amount was found to be on the order of 2.5 to 10%;
(3) the inclusion in the destabilizing solvent of a destabilizing agent (such as ethanol or detergent) in an amount that destabilizes but does not disrupt the preformed lipid vesicles; and
(4) performing the assembly of the fully lipid-encapsulated therapeutic agent particles at a temperature where the aggregation and the entrapment step are not decoupled.

In general this will require operation in a temperature range of room temperature (~20° C.) or above, depending on the concentration of destabilizing agent and the lipid composition.

The method of the invention can be practiced using conventional mixing apparatus. For large scale manufacture, however, it may be desirable to use a specifically adapted apparatus which is described in a concurrently filed PCT application, entitled "Methods and Apparatus for Preparation of Lipid Vesicles", PCT/CA00/00842, filed 14 Jul. 2000, which is incorporated herein by reference.

The method of the invention will now be further described with reference to the following, non-limiting examples.

EXAMPLES

Materials Used in the Following Examples are Supplied as Follows:

The phosphorothioate antisense oligodeoxynucleotides and plasmid DNA used in this study were provided by Inex Pharmaceuticals (Burnaby, BC, Canada). The mRNA targets and sequences of the oligonucleotides are as follows:
human c-myc, 5'-TAACGTTGAGGGGCAT-3' (Seq ID No. 1);
human ICAM-1, 5'-GCCCAAGCTGGCATCCGTCA-3' (SEQ ID No. 2); and
FITC-labeled human EGFR, 5'-CCGTGGTCATGCTCC-3' (SEQ ID No. 3).

1,2-Distearoyl-sn-glycero-3-phosphocholine (DSPC) was purchased from Northern Lipids (Vancouver, BC, Canada) and 1,2-dioleoyl-3-dimethylammoniumpropane (DODAP), 1,2-dioleoyl-sn-glycero-3-phosphoserine-N-(7-nitro-2-1,3-benzoxadiazol-4-yl) (NBD-PS), 1,2-dioleoyl-sn-glycero-3-phosphoethanolamine (DOPE), 1,2-dioleoyl-sn-glycero-3-phosphoethanolamine-N-(lissamine rhodamine b sulfonyl) (LRh-PE) as well as 1,2-dioleoyl-sn-glycero-3-phosphoethanolamine-N-(7-nitro-2-1,3-benzoxadiazol-4-yl) (NBD-PE) from Avanti Polar Lipids (Alabaster, Ala.). 1-Hexadecanoyl-2-(1-pyrenedecanoyl)-sn-glycero-3-phosphocholine (Py-HPC) and the oligonucleotide-binding dye OliGreen were obtained from Molecular Probes (Eugene, Oreg.). 1-O-(2'-(ω-methoxypolyethylene-glycol)succinoyl)-2-N-myristoylsphingosine (PEG-CerC$_{14}$), radioactively labeled [$^3$H]-PEG-CerC$_{14}$ as well as 1-O-(2'-(ω-methoxypolyethylene-glycol)succinoyl)-2-N-dodecanoylsphingosine (PEG-CerC$_{20}$) were provided by INEX Pharmaceuticals (Burnaby, BC, Canada). Cholesterol (chol), n-octyl β-D-glucopyranoside (OGP), Triton X-100, calcein, dichlorodimethylsilane, sodium hydrosulfite (dithionite), 2-p-toluidinylnaphthalene-6-sulfonate (TNS) and polyanetholesulfonic acid (PASA) were obtained from Sigma (Oakville, ON, Canada). All materials for transmission electron microscopy including osmium tetroxide, lead citrate, maleic acid, sodium cacodylate and the embedding resin Embed 812 were purchased from Electron Microscopy Sciences (Fort Washington, Pa.) and low melting point (L.M.P.) agarose from Life Technologies (Burlington, Ontario). Cholesterol (CHOL) was purchased from Sigma Chemical Company (St. Louis, Mo., USA). PEG-ceramides were synthesized by Dr. Zhao Wang at Inex Pharmaceuticals Corp. using procedures described in PCT WO 96/40964, incorporated herein by reference. [$^3$H] or [$^{14}$C]-CHE was purchased from NEN (Boston, Mass., USA). All lipids were >99% pure. Ethanol (95%), methanol, chloroform, citric acid, HEPES and NaCl were all purchased from commercial suppliers.

Analytical Methods: Assays employed to determine if a lipid-therapeutic agent is "encapsulated" such as being "fully encapsulated" are set out in WO 98/51278, and incorporated herein by reference. Such methods include S1 Nuclease Digestion, Serum Nuclease, and Micrococcal Nuclease analysis.

The Oligreen Assay was used to quantify the amount of oligonucleotide loaded into the vesicles. A fluorescent dye binding assay for quantifying single stranded oligonucleotide in aqueous solutions was established using a Biolumin™ 960 fluorescent plate reader (Molecular Dynamics, Sunnyvale, Calif., USA). Briefly, aliquots of encapsulated oligonucleotide were diluted in HEPES buffered saline (HBS; 20 mM HEPES, 145 mM NaCl, pH 7.5). A 10 μL aliquot of the diluted sample was added to 100 μL of a 1:200 dilution of Oligreen™ reagent, both with and without 0.1% of Triton X-100 detergent. An oligo standard curve was prepared with and without 0.1% Triton X-100 for quantification of encapsulated oligo. Fluorescence of the Oligreen™-antisense complex was measured using excitation and emission wavelengths of 485 nm and 520 nm, respectively. Surface associated antisense was determined by comparing the fluorescence measurements in the absence and presence of detergent.

Dynamic light scattering. Sizes were determined by dynamic light scattering using a NICOMP 370 particle sizer (Nicomp Particle Sizing Inc., Santa Barbara, Calif.). Throughout the application, number-averaged sizes are presented, which were obtained by a cumulant fit from the experimental correlation functions. The polydispersity is expressed as the half-width at half-height of a monomodal Gaussian size distribution. The viscosity of the ethanol/citrate buffer was determined using an Ubelohde-type viscometer (Cannon 50). The viscosity of ethanol/300 mM citrate buffer (40/60 (v/v)) at 23° C. measured relative to water at the same temperature was found to be 2.674 mPa*s. The zeta potential was determined by electrophoretic light scattering using a Coulter light scattering instrument (DELSA, Coulter Electronics Inc., FL).

Lipid flip-flop. Lipid flip-flop was determined by chemical reduction of the fluorescent lipid, NBD-PS, to a non-fluorescent compound with sodium dithionite (McIntyre and Sleight, 1991; Lentz et al., 1997). Liposomes were prepared at 20 mM lipid by extrusion in the presence of 1 mol % NBD-PS. Only NBD-PS located in the outer monolayer is accessible to the reducing agent, dithionite, added to the external medium. Its redistribution from the inner monolayer to the outer can be followed after reduction of NBD-PS in the outer membrane leaflet. A 1 M sodium dithionite solution was freshly prepared in 1 M TRIS. NBD-PS in the outer monolayer was reduced by addition of a 100-fold molar excess of sodium dithionite relative to NBD and incubation for 10 min. The completion of the reaction was checked by measuring the dithionite fluorescence at 520 nm before and after reduction exciting at 465 nm. Excess dithionite was subsequently removed by size exclusion chromatography on a Sephadex G50 column. The liposomes were incubated in the presence of 40% ethanol and aliquots corresponding to a final lipid concentration of 150 µM removed for measurement at different time points.

Leakage experiments. Ethanol-induced permeabilization of LUVs was measured at different temperatures and as a function of the size (MW) of the entrapped solute. Calcein was used as a low molecular weight marker for leakage and FITC-dextran (MW 19500) as a high molecular weight marker. Leakage of calcein entrapped at self-quenching concentrations was followed by monitoring the dequenching of the calcein fluorescence. LUVs were prepared by hydration of a lipid film with an aqueous solution containing 75 mM calcein and 5 mM HEPES adjusted to pH 7.5 by addition of sodium hydroxide, followed by 5 freeze/thaw cycles and extrusion through 2 stacked 100 nm filters (10 passes). In the case of DSPC/chol/PEG-CerC$_{14}$/DODAP extrusion was performed at 60° C. Unentrapped calcein was exchanged against an isoosmotic HBS buffer by anion exchange chromatography on a DEAE Sepharose CL6B column. The liposome stock solution was diluted to a lipid concentration of 3 µM in HBS containing varying amounts of ethanol pre-equilibrated at 25, 40 or 60° C. The fluorescence at 520 nm was measured (excitation wavelength 488 µm, long-pass filter at 430 nm) with a Perkin Elmer LS50 Fluorimeter (Perkin Elmer) after 5 min of incubation at the corresponding temperature. The value for 100% leakage (maximum dequenching) was obtained by addition of a 10% Triton X-100 solution to a final concentration of 0.05%. Calcein leakage was calculated according to % leakage=$(F_s-F_b)/(F_{Tx}-F_b)*100$, where $F_s$ is the fluorescence of the sample, $F_b$ the background corresponding to calcein containing liposomes in the absence of ethanol and $F_{Tx}$ the Triton X-100 value.

FITC-dextran (MW 19500) was entrapped in DSPC/Chol/PEG-CerC$_{14}$/DODAP liposomes incorporating 0.5 mol % LRh-PE at a final concentration of 45 mg/ml. Entrapment was performed by addition of the lipids dissolved in ethanol to the FITC-dextran solution in HBS followed by extrusion (2 stacked 100 nm filters, 2 passes) and subsequent removal of ethanol by dialysis. Unentrapped FITC-dextran was removed by size exclusion chromatography on a Sepharose CL4B column (1.5×15 cm). The loss of FITC-dextran from liposomes exposed to 40% ethanol was determined after removal of released FITC-dextran by size exclusion chromatography on a Sepharose CL4B column (1.5×15 cm). The FITC/LRh-PE ratio was measured before and after addition of ethanol. FITC and LRh-PE fluorescence were measured at 515 nm and 590 nm with the excitation wavelength set to 485 nm and 560 nm, respectively.

Lipid mixing. Ethanol-induced lipid mixing/exchange was followed by the loss of resonance energy transfer, occuring between a donor, NBD-PE, and an acceptor, LRh-PE, which are in close proximity, upon dilution of the probes into an unlabeled target membrane (Struck et al., 1981). LUVs contained 0.75 mol % of both NBD-PE and LRh-PE. Labeled and unlabeled liposomes were prepared in HBS pH 7.5 by extrusion at lipid concentrations of 20 mM. Ethanol was added to labeled and unlabeled liposomes to a final concentration of 40% (v/v). Subsequently, the ethanolic dispersions of labeled and unlabeled liposomes were mixed at a molar lipid ratio of 1:5 and incubated at the appropriate temperatures. Aliquots were withdrawn at given time-points and added to 2 ml of HBS to give a final lipid concentration of 150 µM. Emission spectra of NBD and LRh were measured in the region from 505 to 650 nm with the excitation wavelength set to 465 nm (430 nm emission long-pass filter). After background subtraction (unlabeled liposomes at 150 µM lipid) the loss of resonance energy transfer was expressed as the increase in NBD/LRh ratio.

Pyrene-HPC assay. Pyrene-HPC forms excited state dimers at high concentrations, which fluoresce at a different wavelength than the monomers. Excimer formation is a diffusion-controlled process and requires two molecules to come together to form a dimer. Lipid mixing (target membrane) as well as a decrease in the lateral mobility of pyrene-HPC in the membrane can result in a decrease in pyrene excimer fluorescence (Hoekstra, 1990; Duportail and Lianos, 1996). Lateral phase separation usually results in an increase in pyrene excimer fluorescence (Duportail and Lianos, 1996). The rationale of this experiment was to look at the effect of oligonucleotide binding on the liposomal membrane. The pyrene-HPC fluorescence of liposomes entrapping oligonucleotide was compared to empty control liposomes before and after depletion of the transmembrane pH gradient. Increasing the internal pH to 7.5 results in the release of membrane-bound oligonucleotides. Liposomes incorporating pyrene-HPC at a concentration of 7 mol % were prepared by addition of lipids dissolved in ethanol to pH 4 citrate buffer. An aliquot was removed and oligonucleotide entrapped as described above. The remaining initial liposomes were treated the same way in all the subsequent steps (see under entrapment). The pH gradient was dissipated with ammonium acetate adjusted to pH 7.5. Liposomes were diluted into the appropriate buffer, HBS pH 7.5 or 150 mM ammonium acetate pH 7.5, to a final lipid concentration of 2 µM. Pyrene-HPC emission spectra were recorded in the wavelength region from 365–550 nm with excitation at 345 nm and an emission cut-off filter at 350 nm. The intensity ratio of monomer fluorescence at 397 nm to dimer fluorescence at 478 nm was plotted for the initial liposomes as well as for the oligonucleotide containing liposomes before and after depletion of the pH gradient.

$^{31}$P NMR Spectroscopy. $^{31}$P NMR spectra were obtained with a Bruker MSL200 spectrometer operating at 81 MHz. Free induction decays (FIDs) corresponding to 800 or 2400 scans were collected by using a 2.8 µs 50° pulse with a 3 sec interpulse delay and a spectral width of 20000 Hz on a 2.0 ml sample in a 10 mm probe. No proton decoupling was employed. An exponential multiplication corresponding to 25 Hz of line broadening was applied to the FIDs prior to Fourier transformation. The chemical shift was referenced to external 85% phoshoric acid ($H_3PO_4$). The spin-lattice relaxation times ($T_1$) of free and encapsulated oligonucleotides at pH 7.5 are essentially the same with $T_1^{free}$=1.7 sec and $T_1^{enc.}$=2.1 sec. The $T_1$-values were measured by an inversion-recovery pulse sequence. The interpulse delay of 3 sec for 50° pulses allows for complete relaxation of all antisense resonances.

Ultracentrifugation. Liposomes with and without entrapped oligonucleotides were fractionated by ultracentrifugation on a sucrose step gradient consisting of 1%, 2.5%, 10% and 15% (w/v) sucrose in HBS pH 7.5 with a step volume of 3.5, 3.5, 2.5 and 1.5 ml, respectively. Samples were centrifuged for 2 hrs at 36000 rpm ($RCF_{Rmax}$ 221000xg) using a Beckmann L8-70 ultracentrifuge in combination with a SW41 Ti rotor. The gradient was either fractionated from the top or individual bands were removed with a syringe after puncturing the tube with a needle.

Cryo-Transmission Electron Microscopy (cryo-TEM). A drop of sample was applied to a standard electron microscopy grid with a perforated carbon film. Excess liquid was removed by blotting with filter paper leaving a thin layer of water covering the holes of the carbon film. The grid was rapidly frozen in liquid ethane, resulting in vesicles embedded in a thin film of amorphous ice. Images of the vesicles in ice were obtained under cryogenic conditions at a magnification of 66000 and a defocus of −1.5 micron using a Gatan cryo-holder in a Philips CM200 FEG electron microscope.

Freeze-Fracture Electron Microscopy. Samples were cryofixed in the presence of 25% glycerol by plunging them into liquid Freon 22 cooled by liquid $N_2$. The fractured surface was shadowed unidirectionally with platinum (45°) and coated with carbon (90°) employing a Balzers Freeze-Etching system BAF 400D (Balzers, Liechtenstein). Replicas were analyzed using a JEOL Model JEM 1200 EX electron microscope (Soquelec, Montreal, QC, Canada).

Transmission Electron Microscopy (TEM). Vesicles were fixed by the addition of 1 volume of 2% osmium tetroxide to 0.5 volumes of vesicles in HBS followed by centrifugation at 17000×g and 4° C. for 45 min. The resulting pellet was mixed with an equal volume of 3% agarose/PBS, pipetted onto a microscope slide and allowed to cool to 4° C. The solidified agarose containing the vesicles was cut into 1 mm pieces and transferred to a glass tube for further processing. The blocks were washed for 3×5 min with 0.05 M maleic acid pH 5.2 before staining in 2% uranyl acetate for 1 h. The tissue pieces were dehydrated through a graded series of alcohols (50–100%), infiltrated with increasing ratios of epoxy resin (EMbed 812):propylene oxide and embedded in 100% EMbed 812 at 60° C. for 24 h. Ultrathin sections were stained with 2% lead citrate and examined using a Zeiss EM 10C transmission electron microscope (Oberkochen, Germany).

Phase contrast and fluorescence microscopy. Phase contrast and fluorescence microscopy were performed on a Zeiss Axiovert 100 microscope using a Plan Apochromat 63x/1.4NA oil immersion objective in combination with a 1.6× optovar lens and a XF100 filter set from Omega Optical (Brattleboro, Vt.) with the following optical specifications: excitation 475±20/dichroic 500/emission 535±22.5. Images were recorded on Kodak Ektachrome P1600 color reversal film at 1600 ISO with a Zeiss MC80 DX microscope camera. Slides and coverglasses were siliconized with dichlorodimethylsilane to neutralize the otherwise negatively charged glass surface.

Example 1

Empty preformed vesicles were prepared from a lipid mixture containing PEG-CerC14, DODAP, DPSC and CHOL in a molar ratio of 5:25:25:45. The four lipids were dissolved in a 100% ethanol to a total lipid concentration of 25 mg/ml (33 mM). The ethanolic lipid was then introduced through an injection port with an orifice diameter of 0.25 mm into a reservoir containing 300 mM citrate buffer, pH 4.0. The reservoir and all solutions were at room temperature. The total volume of ethanolic lipid was 6 liters, and the flow rate for lipid introduction was 200–300 ml/min. The total volume of citrate buffer was 9 liters. The resulting 15 liter mixture had an ethanol concentration of 40% and 180 mM citrate. Vesicles of 170±20 nm median diameter were generated. The empty preformed vesicles were sized to 90–120 nm median diameter by 1–3 passes through the extrusion circuit (65° C.) at low pressure (100 p.s.i., reduced from classical 500–1000 p.s.i.) using two stacked 80 nm membranes. The empty preformed vesicles were then pooled in a reservoir 20 and maintained at 40° C. until addition of therapeutic agent solution.

Example 2

Preformed vesicles of example 1 were used to make fully lipid-encapsulated therapeutic agent particles using oligonucleotide INX-6295 (Seq. ID No. 1) as the therapeutic agent. Oligonucleotide INX-6295 in distilled water was diluted by the addition of 100% ethanol to form a various solutions of 10, 20, 30 40 or 50 mg/ml oligonucleotide in 40% ethanol. The ethanolic oligonucleotide was added to the preformed vesicles in reservoir 20 at 40° C. with gentle mixing. The amount and volume of ethanolic oligonucleotide was calculated to provide a final drug:lipid ratio of 0.1 to 0.25 by weight. The mixture was then incubated at 40° C. with gentle and periodic mixing for 1 hour. After incubation, the solution was processed by diafiltration to strip free or excess associated oligonucleotide, remove ethanol and exchange the buffer system to phosphate buffered saline (PBS), pH 7.4. Concentration, sterile filtration and packaging complete the preparation of a commercial product.

Example 3

The procedure of Example 2 was repeated with changes to various parameters to determine which might be critical to the preparation of fully lipid-encapsulated therapeutic agent particles in accordance with the invention. In these experiments, the total oligonucleotide recovery (yield), the total lipid recovery (yield) and the encapsulation efficiency were considered as indications of the quality of the product and the process. Total oligonucleotide recovery was calculated using the formula:

$$\frac{\text{final oligo concentration (mg/ml)} \times \text{final volume (ml)}}{\text{initial oligo concentration (mg/ml)} \times \text{initial volume (ml)}} \times 100\%$$

Total lipid recovery was calculated using the formula:

$$\frac{\text{final lipid concentration (mg/ml)} \times \text{final volume (ml)}}{\text{initial lipid concentration (mg/ml)} \times \text{initial volume (ml)}} \times 100\%$$

Encapsulation Efficiency (E.E.) was calculated using the formula:

$$\frac{\text{initial oligo (mg/ml)}/\text{initial lipid (mg/ml)}}{\text{final oligo (mg/ml)}/\text{final lipid (mg/ml)}} \times 100\%$$

The percentage of oligo that is encapsulated (i.e., incorporated in bilayers or entrapped in the interior of the lipid particle) was determined with the OliGreen assay described above.

To assess the significance of the initial drug to lipid ratio, the experiment was conducted with two different starting ratios. The results are summarized in Table 1. No change in the size of the vesicles was observed in the process of loading the oligonucleotide.

TABLE 1

| Initial Drug/Lipid Ratio | Oligo Yield % | Lipid Yield % | Encap Oligo % | Vesicle size (nm) | Final Drug/Lipid Ratio | E.E. % |
|---|---|---|---|---|---|---|
| 0.1 | 80–90 | 70–80 | ≧90 | 106 | 0.1 | 100 |
| 0.2 | 60–78 | 70–75 | ≧80 | 119 | 0.17–0.2 | 85–100 |

To assess the significance of incubation temperature, the experiment was conducted at room temperatures and at two elevated temperatures for 1 hour. The results are summarized in Table 2. As shown, the higher temperature of 60° C. begins to impair the efficiency of the process, and to lead to an increase in particle size. Thus, lower temperatures are preferred.

TABLE 2

| Incubation Temp (° C.) | Oligo Yield % | Encaps Oligo % | Vesicle Size (nm) |
|---|---|---|---|
| RT(20–22) | 73 | 90 | 114 |
| 40 | 84 | 91 | 109 |
| 60 | 52 | 83 | 140 |

To assess the significance of incubation time, the experiment was conducted at three incubation times and an incubation temperature of 40° C. The results are summarized in Table 3. As shown, the yield improves between 0.5 hours and 1 hour, but increased incubation time beyond an hour does not result in a substantial improvement. Thus, the most efficient process in the apparatus used will employ an incubation time of about 1 hour.

TABLE 3

| Incubation time (hr) | Oligo Yield % | Encapsulated Oligo % |
|---|---|---|
| 0.5 | 22 | 92 |
| 1 | 60 | 94 |
| 2 | 56 | 95 |

To assess the significance of buffer concentration in the oligonucleotide solution, the experiment was conducted at four different concentrations of citrate buffer and an initial drug/lipid ratio of 0.1. The results are summarized in Table 4.

TABLE 4

| Citrate Buffer Conc (mM) | Oligo Yield % | Encapsulated Oligo % | Vesicle Size (nm) |
|---|---|---|---|
| 50 | 100 | 94 | 80 |
| 100 | 88 | 90 | 90 |
| 200 | 89 | 91 | 93 |
| 300 | 80–90 | 92 | 106 |

To assess the significance of the initial ethanol concentration during the mixing step, the experiment was conducted with 3 different initial ethanol concentrations at each of two initial drug to lipid ratios. The results are summarized in Table 5. There appears to be an optimum ethanol concentration which is different for each starting oligo/lipid ratio. In an addition experiment not reported in the Table, an initial ethanol concentration of 50% was used with an oligo/lipid ratio of 0.1. Significant problems of unknown cause were encountered in this experiment and no yield of product was obtained.

TABLE 5

| Initial EtOH % | Initial Drug/Lipid | Oligo Yield % | Encaps Oligo % | Vesicle size (nm) | Final Drug/Lipid | E.E. % |
|---|---|---|---|---|---|---|
| 33 | 0.2 | 42–47 | 88 | 115 | 0.12 | 60 |
| 40 | 0.2 | 70 | 82 | 114 | 0.15 | 75 |
| 43 | 0.2 | 64 | 62 | 105 | 0.19 | 95 |
| 36 | 0.1 | 52–66 | 85–89 | 110 | nd | nd |
| 43 | 0.1 | 90–100 | 84–89 | 116 | nd | nd |
| 45 | 0.1 | 90–100 | 90–92 | 108 | nd | nd |

To assess the significance of initial oligonucleotide concentration (and thus of the volume of therapeutic agent solution to obtain the same initial drug to lipid ratio), stock solutions at four different concentrations of oligonucleotide were used. The results are summarized in Table 6. As shown, this parameter does not appear to be critical to the results obtained using the method of the invention.

TABLE 6

| Oligo Stock mg/ml | Initial Drug/Lipid | Oligo Yield % | Encaps Oligo % | Vesicle Size (nm) |
|---|---|---|---|---|
| 10 | 0.1 | 85 | 90 | 106 |
| 20 | 0.1 | 80 | 88 | 112 |
| 30 | 0.1 | 87 | 90 | 110 |
| 40–50 | 0.1 | 80–90 | 88–94 | 106 |

Example 4

To demonstrate the applicability of the invention to larger therapeutic agents, plasmid pINEX L1018, a 5.5 kb plasmid encoding the luciferase gene linked to a CMV promoter, and also carrying SV40 enhancer elements and an AmpL gene was loaded into preformed lipid vesicles.

Preformed lipid vesicles were prepared by slowly adding 10 mg of lipids (DSPC/Chol/.DODAP/PEG-CerC14 in a 20/45/25/10 mol % ratio) dissolved in 100% ethanol to 25 mM citrate buffer (25 mM citric acid, 255 mM sucrose, adjusted to pH 4 with sodium hydroxide). Both solutions were prewarmed to 40° C. before mixing. The final ethanol concentration was 40% (v/v). The ethanolic dispersion of lipid vesicles was extruded 2× through 2 stacked 100 nm polycarbonate filters at room temperature. 0.25 mg of plasmid DNA in 40% ethanol was added to the lipid vesicles at room temperature, followed by a 1 hour incubation of the sample at 40° C. The initial plasmid/lipid ratio was 0.025. Subsequently, the sample was dialyzed against 2 L of 25 mM saline, pH 7.5 (20 mM HEPES, 150 mM NaCl) for a total of 18–20 hours.

Trapping efficiency was determined after removing remaining external plasmid DNA by anion exchange chromatography on a DEAE Sepharose CL6B column. Plasmid DNA was quantified using the DNA Binding System PicoGreen lipid by inorganic phosphate assay according to Fiske and Subbarrow after separation from the plasmid by a Bligh Dyer extraction. In addition, the final lipid concentration was determined by incorporating 0.25 mol % of the fluorescently-labeled lipid Lissamine rhodamine-PE in the lipid vesicles.

The final plasmid lipid ratio was 0.022, which corresponds to 88% entrapment. The resulting lipid-encapsulated therapeutic agent particles had an average size of 100 nm and a very small size distribution.

Example 5

20 Liposome preparation: Large unilamellar liposomes in ethanol/buffer solutions were either prepared by addition of ethanol to extruded liposomes or by addition of lipids dissolved in ethanol to an aqueous buffer solution and subsequent extrusion. Both methods give the same entrapment results and will be described in greater detail in the following:

1. After hydration of a lipid film in pH 4 citrate buffer and 5 freeze/thaw cycles LUVs were generated by extrusion through 2 stacked 100 nm filters (10 passes). In the case of DODAP/DSPC/Chol/PEG-CerC14 liposomes the extrusion was performed at 60° C. Ethanol was subsequently slowly added under rapid mixing. Typical liposome sizes determined after removal of ethanol by dynamic light scattering were 90±20 nm for the DODAP/DSPC/Chol/PEG-CerC$_{14}$ system. Slow addition of ethanol and rapid mixing are important as liposomes become unstable and coalesce into large lipid structures as soon as the ethanol concentration exceeds a certain upper limit. The latter depends on the lipid composition. For example, an initially translucent DSPC/Chol/PEG-CerC$_{14}$/DODAP liposome dispersion becomes milky white if the ethanol concentration exceeds 50% (v/v).

2. LUVs were prepared by slow addition of the lipids dissolved in ethanol (0.4 ml) to citrate buffer at pH 4 (0.6 ml) followed by extrusion through 2 stacked 100 nm filters (2 passes) at RT. Dynamic light scattering measurements performed in ethanol and after removal of ethanol by dialysis show no significant differences in size, which is typically 75±18 nm. The extrusion step can be omitted if ethanol is added very slowly under vigorous mixing to avoid locally high ethanol concentrations.

Entrapment procedure. An oligonucleotide solution was slowly added under vortexing to the ethanolic liposome dispersion, which was subsequently incubated at the appropriate temperature for 1 hr, dialyzed for 2 hrs against citrate buffer to remove most of the ethanol and twice against HBS (20 mM HEPES/145 mM NaCl, pH 7.5). At pH 7.5 DODAP becomes charge-neutral and oligonucleotides bound to the external membrane surface are released from their association with the cationic lipid. Unencapsulated oligonucleotides were subsequently removed by anion exchange chromatography on DEAE-sepharose CL-6B columns equilibrated in HBS pH 7.5. When octylglucoside was used in place of ethanol the detergent was added to liposomes (1:1 v/v) to final concentrations ranging from 30–40 mM. All the subsequent steps were performed as described above except for the initial dialysis step against pH 4 citrate buffer, which was extended to 5 hrs. In the following examples, if not otherwise mentioned, DSPC/Chol/PEG-CerC$_{14}$/DODAP liposomes (20:45:10:25 mol %), c-myc (Seq. ID No. 1), 40% (v/v) ethanol, 300 mM citrate buffer and incubation at 40° C. were used.

Determination of trapping efficiencies: Trapping efficiencies were determined after removal of external oligonucleotides by anion exchange chromatography. Oligonucleotide concentrations were determined by UV-spectroscopy on a Shimadzu UV160U spectrophotometer. The absorbance at 260 nm was measured after solubilization of the samples in chloroform/methanol at a volume ratio of 1:2.1:1 chloroform/methanol/aqueous phase (sample/HBS). If the solution was not completely clear after mixing an additional 50–100 µl of methanol was added. Alternatively, absorbance was read after solubilization of the samples in 100 mM octylglucoside. The antisense concentrations were calculated according to: c [µg/µl]=A$_{260}$*1 OD$_{260}$ unit [µg/µl]*dilution factor [µg/µl], where the dilution factor is given by the total assay volume [ml] divided by the sample volume [µl]. OD$_{260}$ units were calculated from pairwise extinction coefficients for individual deoxy-nucleotides, which take into account nearest neighbor interactions. 1OD corresponds to 30.97 µg/ml c-myc (Seq. ID. No 1), 33.37 µg/ml h-ICAM-1 (Seq. ID No. 2) and 34 µg/ml EGFR (Seq. ID No. 3). Lipid concentrations were determined by the inorganic phosphorus assay after separation of the lipids from the oligonucleotides by a Bligh and Dyer extraction (Bligh and Dyer, 1959). Briefly, to 250 µl of aqueous phase (sample/HBS) 525 µl methanol and 250 µl chloroform were added to form a clear single phase (aqueous phase/methanol/chlorofrom 1:2.1:1 vol). If the solution was not clear a small amount of methanol was added. Subsequently, 250 µl HBS and an equal volume of chloroform were added. The samples were mixed and centrifuged for 5–10 min at 3000 rpm. This resulted in a clear two-phase system. The chloroform phase was assayed for phospholipid content according to the method of Fiske and Subbarrow (1925). If not otherwise mentioned, trapping efficiencies were expressed as oligonucleotide-to-lipid weight ratios [w/w].

Example 6

Following the procedures of Example 5, increasing amounts of ethanol were added to 100 nm DSPC/Chol/DODAP liposomes (no modified lipid component) prepared by extrusion. All samples became milky white immediately upon oligonucleotide addition, indicating oligonucleotide-induced aggregation. Following incubation with antisense oligonucleotides at a molar ODN/lipid ratio of 0.035 at pH 4, ethanol and unentrapped oligonucleotides were removed. Table 7 lists encapsulation efficiencies as determined by dynamic light scattering, together with the final sizes of the resulting multilamellar vesicles. Increasingly more antisense oligonucleotide becomes entrapped as the ethanol concentration is increased. The concomitant increase in size and polydispersity reflects a progressive reorganization of the LUVs into larger lipid structures, which appear to be predominantly large multilamellar liposomes. It should be noted that due to the size of these systems some of the lipid is lost on the anion exchange column used to remove external unentrapped oligonucleotides. The eluted fraction corresponds to roughly 50–60% of total lipid. At ethanol concentrations of 40% and higher the initial liposomes become unstable and fuse to form a milky white dispersion.

TABLE 7

| % EtOH [v/v] | % encapsulation | Average size [nm] |
|---|---|---|
| 0 | 4.4 | 148 ± 56 |
| 20 | 20.5 | 226 ± 104 |
| 30 | 32.5 | 470 ± 244 |
| after extrusion | (no antisense) | 99 ± 22 |

These results demonstrate that ethanol makes the lipid membranes susceptible to structural rearrangements which lead lead to entrapment of the oligonucleotide between the concentric lamellae of large multilamellar liposomes. However, the size of resulting liposomes cannot be readily controlled.

Example 7

Figure 2:
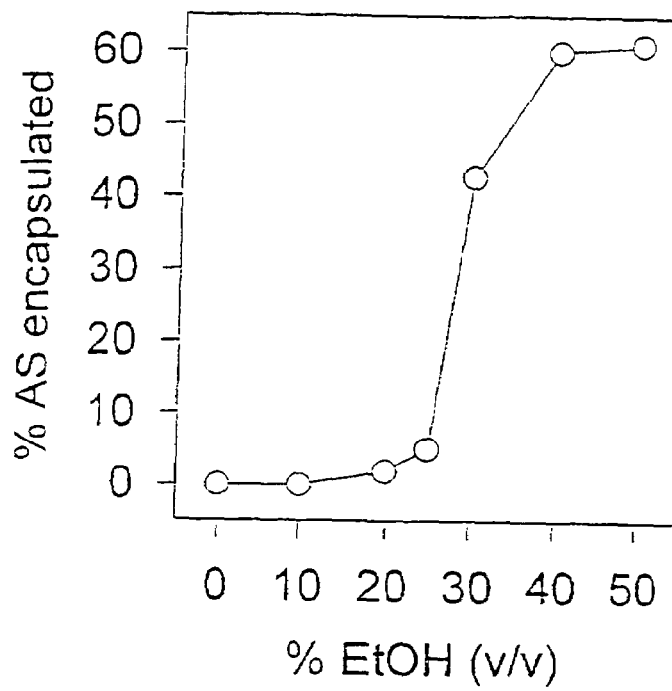
FIG. 2 depicts encapsulation efficiencies as a function of ethanol concentration for liposomes containing 10 mol % PEG-Cer.

Liposomes were made containing 2.5 to 10 mol % of modified lipid (PEG-Cer) and tested using the protocols of Examples 5 and 6. In each case, the decrease in PEG-Cer concentration was made up with an increase in DPSC levels. It was found that the incorporation of the modified lipid into the liposomes allows the final size of the antisense-containing liposomes to be regulated. Liposomes were stable at higher ethanol concentrations in the presence of PEG-Cer than in its absence. The dispersions remained optically translucent in 40% ethanol, although a slight increase in turbidity was noted for the sample containing 2.5 mol % PEG-Cer. The increased stability is also reflected in the higher amounts of ethanol required for entrapment to occur (Table 8, FIG. 2). FIG. 2 depicts encapsulation efficiencies as a function of ethanol concentration for liposomes containing 10 mol % PEG-Cer. Maximum entrapment was reached at 40% ethanol and ethanol concentrations in excess of 25% (v/v) (>4.3 M) were required for entrapment to occur. No entrapment was found in the absence of ethanol. Table 8 lists trapping efficiencies and sizes determined by dynamic light scattering as a function of PEG-Cer content (2.5–10 mol %) at the minimum and maximum ethanol concentrations determined from FIG. 2. The sizes of the initial extruded liposomes are given in brackets. The amount of ethanol required for entrapment to occur depends on the PEG-Cer content of the liposomes. Liposomes containing 2.5 mol % PEG-Cer entrapped approximately 15% of the oligonucleotides at 25% ethanol and 45% in the presence of 40% ethanol. In contrast, at 10 mol % PEG-Cer entrapment was virtually abolished in the presence of 25% ethanol (<5%) and was 60% in 40% ethanol. In all cases the initial oligonucleotide-to-lipid ratio was 0.037 (mol/mol). Entrapment levels increased from 45% to almost 60% in 40% ethanol when the PEG-Cer content was increased from 2.5 to 10 mol %. Liposome size and polydispersity decreased from 131±40 nm to 100±26 nm.

TABLE 8

| PEG-CerC$_{14}$ [mol %] | % encapsulation | Average size [nm] |
|---|---|---|
| 25% ethanol | | |
| 2.5 | 14.1 | 125 ± 35 (108 ± 26) |
| 10 | 5 | 92 ± 18 (93 ± 18) |
| 40% ethanol | | |
| 2.5 | 45.7 | 131 ± 40 (108 ± 26) |
| 5 | 50.9 | 126 ± 36 (107 ± 22) |
| 10 | 56.5 | 100 ± 26 (93 ± 18) |

Example 8

Figure 3A:
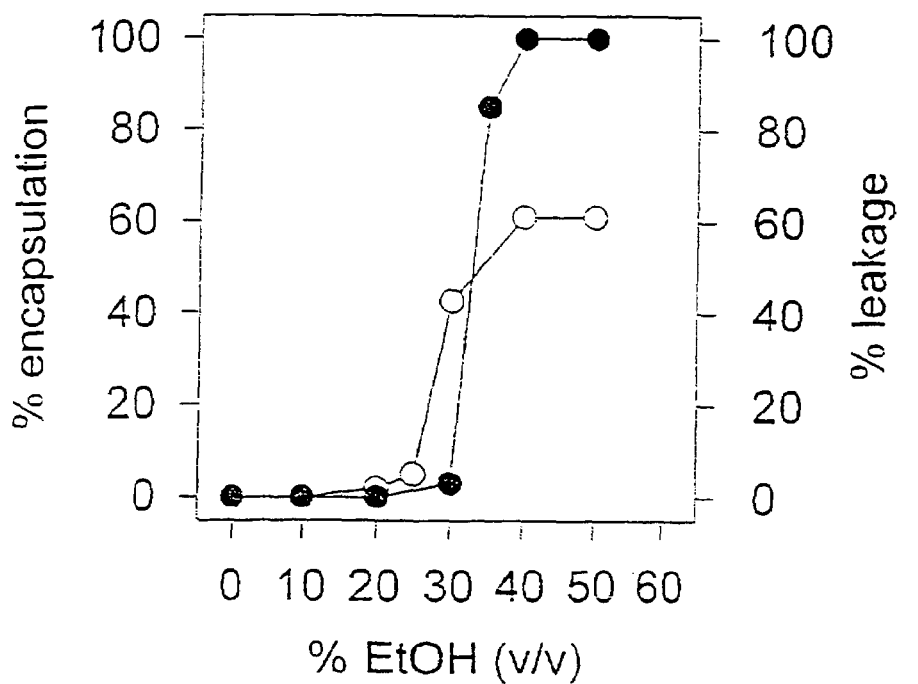
FIG. 3A depicts the release of calcein entrapped at self-quenching concentrations in DSPC/Chol/PEG-CerC$_{14}$/DODAP liposomes as a function of ethanol concentration (closed circles) together with the encapsulation efficiencies obtained using liposomes of the same lipid composition (open circles)

The perturbing effect of ethanol on lipid membranes has been mainly studied at low ethanol concentrations (<15% v/v) in relation to changes in lipid hydration, acyl chain order, membrane permeability to small ions and induction of chain interdigitation in DPPC systems (Slater and Huang, 1988; Barchfeld and Deamer, 1988; Schwichtenhovel et al. 1992; Slater et al., 1993; Barry and Gawrisch, 1994; Vierl et al., 1994; Lobbecke and Cevc, 1995; Komatsu and Okada, 1996; Holte and Gawrisch, 1997). It was logical to ask whether liposomes are still intact at the high ethanol concentrations required for entrapment. FIG. 3A depicts the release of calcein entrapped at self-quenching concentrations in DSPC/Chol/PEG-CerC$_{14}$/DODAP liposomes as a function of ethanol concentration (closed circles) together with the encapsulation efficiencies obtained using liposomes of the same lipid composition (open circles). Both the encapsulation as well as the leakage experiments were performed at 40° C. Leakage of calcein, a small molecule with a MW of 623, starts at ≦30% ethanol and reaches a maximum around 40% ethanol. The oligonucleotide entrapment shows a similar ethanol dependence indicating that the entrapment is highly correlated with the destabilization of the liposomal membrane permeability barrier. In contrast to calcein, the release of FITC-dextran (MW 19500) was less than 10% in 40% ethanol. This shows that the loss of the permeability barrier is MW dependent, as has also been reported for detergents such as octylglucoside (Almog et al., 1990). The liposomes maintained their morphology in the presence of 40% ethanol. Phase contrast microscopy of giant liposomes in 40% ethanol also revealed intact liposomal structures.

Figure 3B:
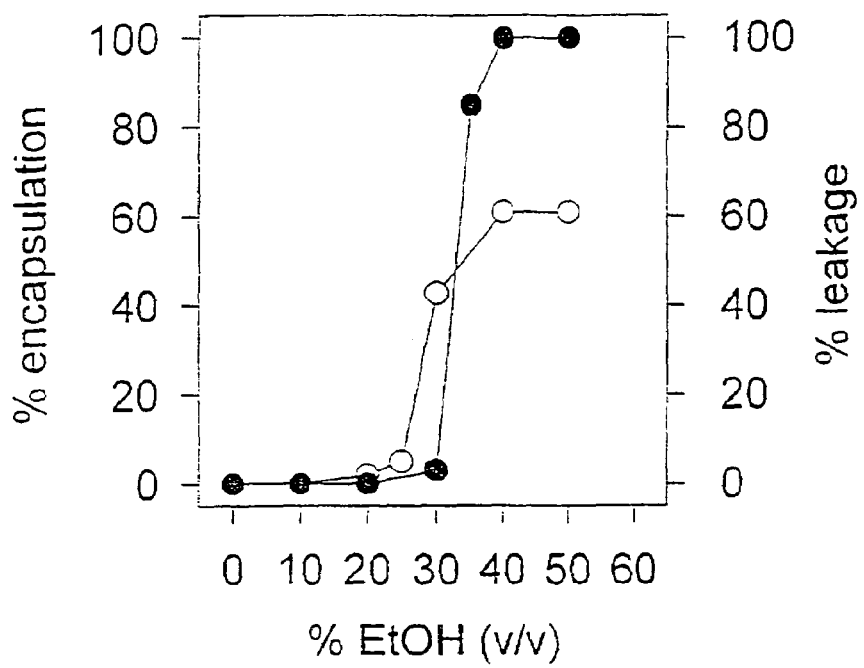
FIG. 3B illustrates rapid exchange of lipids during the formation of lipid entrapped nucleic acids using the method of the invention.

Lipids are also able to exchange rapidly between liposomes and between the inner and outer monolayers of the lipid bilayers comprising the liposomes. As shown in FIG. 3B, lipid mixing as detected by the NBD-PE/LRh-PE FRET assay is effectively immediate in 40% ethanol. No increase in vesicle size was observed indicating the lipid mixing is arising from rapid lipid exchange between liposomes rather than liposome fusion. The results shown in FIG. 3B also demonstrate that lipids are able to rapidly migrate (flip-flop) from one side of the liposomal lipid bilayer to the other, as shown by the of loss in fluorescence of NBD-PS located in the outer lipid monolayer upon chemical reduction with sodium dithionite.

Example 9

Figure 4:
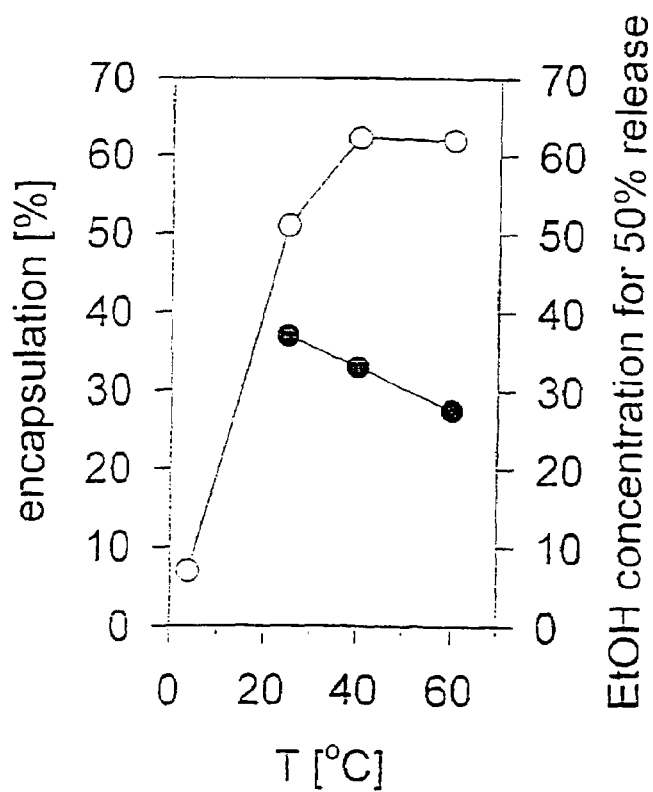
FIG. 4 shows entrapment efficiencies and calcein leakage data plotted as a function of temperature.

The increase in turbidity upon encapsulation indicates that entrapment is preceded by an initial aggregation step (formation of microaggregates). The aggregation step and the entrapment can be decoupled at low temperatures. Samples become turbid upon or shortly after addition of oligonucleotide and the turbidity increases over time. In the absence of ethanol there is only a slight increase in turbidity following which light transmission remains constant. In contrast to samples prepared at 40° C., samples incubated at 4° C. become translucent again when ethanol is removed and liposomes do not entrap oligonucleotide. Entrapment efficiencies are plotted as a function of temperature in FIG. 4 together with calcein leakage data. Leakage data are presented as the ethanol concentrations required to induce 50% calcein release. Again there is a qualitative correlation between the destabilization of the liposomal membrane and the entrapment efficiency.

Example 10

Figure 5:
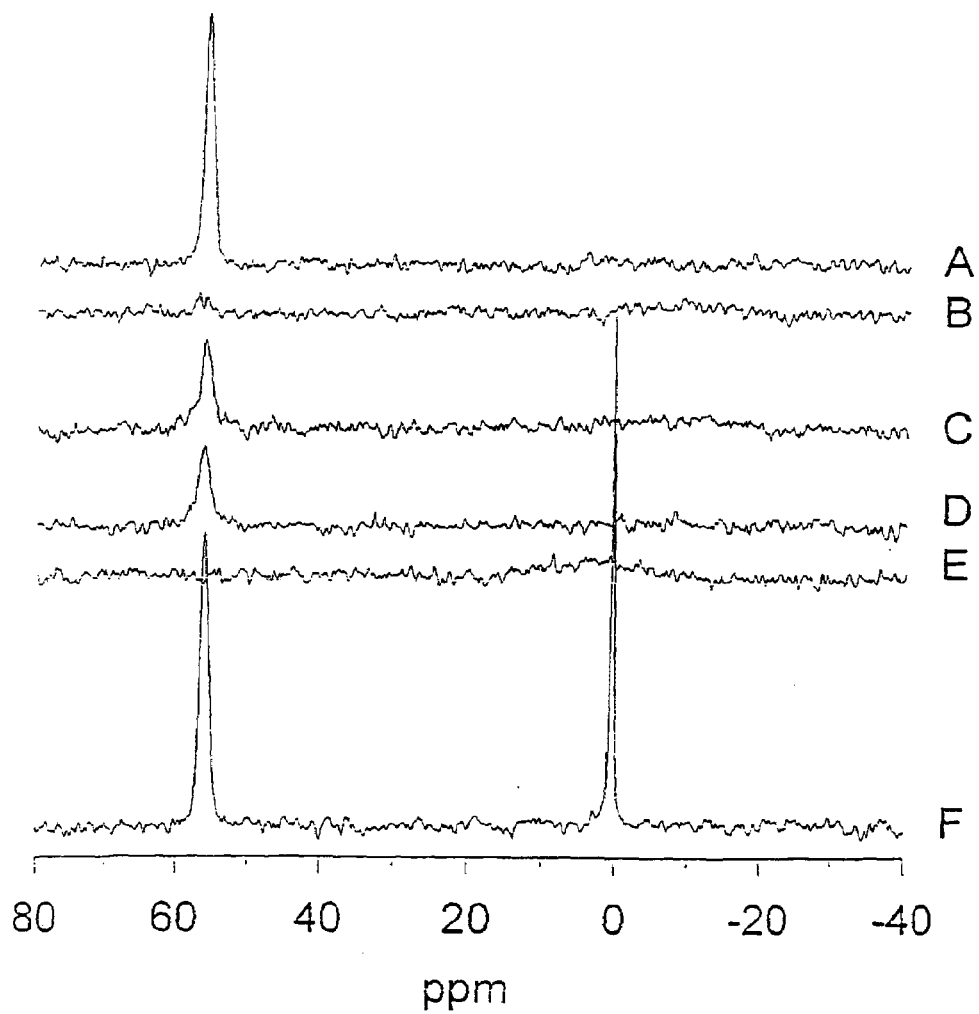
FIG. 5 shows NMR spectra of lipid-associated oligonucleotides.

$^{31}$P-NMR can be used to assay for oligonucleotide entrapment. FIGS. 5A and 5B show $^{31}$P NMR spectra of c-myc in solution (FIG. 5A) and entrapped in DODAP/DSPC/Chol/PEG-CerC$_{14}$ liposomes (FIG. 5B). Initially, the liposomes exhibited a transmembrane pH gradient, where the internal pH is 4 and the external pH 7.5. Under these conditions the entrapped oligonucleotides are tightly associated with the positively charged liposomal membrane.

This immobilization results in the disappearance (broadening out) of the NMR signal (FIG. 5B). Upon dissipation of the pH gradient by addition of ammonium acetate and adjustment of the external pH to 7.5, DODAP is deprotonated and the oligonucleotides dissociate from the liposomal membrane. This is demonstrated by the recovery of the NMR signal in FIG. 5C. However, the recovery is incomplete, about 50% of the initial signal. The signal attenuation is not due to NMR resonance saturation. It may be attributed to two possibilities: either the amount of encapsulated antisense exceeds its solubility so that a portion of it precipitates, or the mobility of the antisense molecules is spatially constrained e.g. by immobilization between two closely apposing bilayers (see FIG. 3A). To confirm that the oligonucleotides were encapsulated and localized in the aqueous interior of the liposomes, 5 mM $MnSO_4$ was added to the external solution (FIG. 5D). $Mn^{2+}$ is a membrane impermeable paramagnetic line broadening agent and will quench the signals of all accessible phosphate groups, phospholipids as well as oligonucleotides. However, the oligonucleotide signal remained unaffected and disappeared only upon solubilization of the liposomes with OGP (FIG. 5E). The whole oligonucleotide signal is recovered when the initial liposomes (FIG. 5B) are solubilized with OGP in the absence of $Mn^{2+}$ (FIG. 5F). These data clearly demonstrate that the oligonucleotide is entrapped in the liposomes and not simply associated with the external membrane. It should also be noted that entrapped oligonucleotides were not accessible to the oligonucleotide-binding dye OliGreen.

The NMR studies describe the interaction between oligonucleotides and liposomes as seen from the perspective of the oligonucleotides. Changes in lipid dynamics and membrane organization can be probed with pyrene-labeled lipids (Duportail and Lianos, 1996). Pyrene-labeled lipids form excited state dimers at high concentrations, which fluoresce at a different wavelength than the monomers. Excimer formation is a diffusion-controlled process and requires two molecules to come together to form a dimer. The binding of the oligonucleotides results in a dramatic reduction of the lateral mobility of all lipid species relative to control liposomes, which do not contain oligonucleotides. The membrane is laterally compressed. This follows from the observed decrease in excimer fluorescence of pyrene-HPC. The depletion of the transmembrane pH gradient results in an increase of the excimer fluorescence and restoration of lipid mobility.

Example 11

Figure 6:
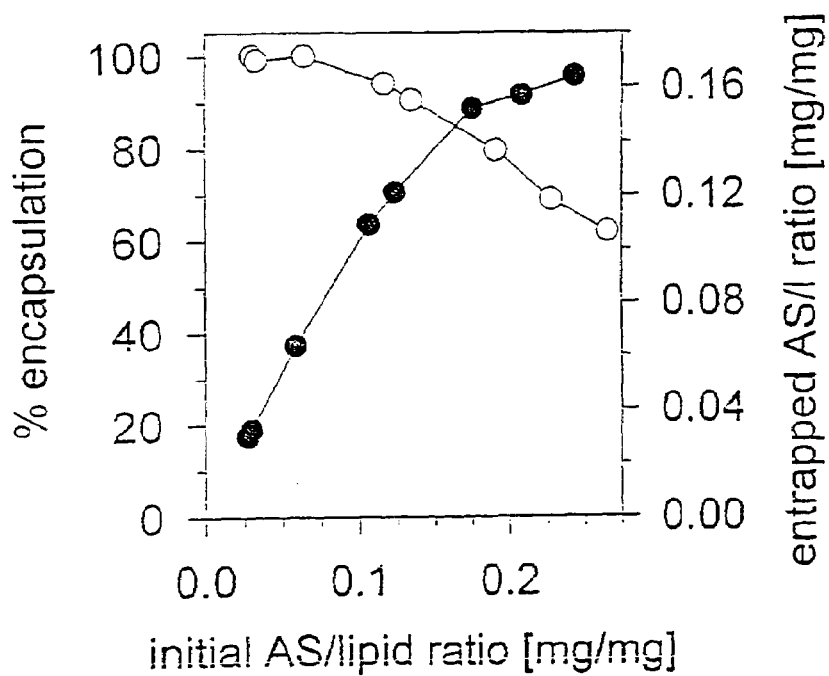
FIG. 6 shows a graph of entrapment efficiency plotted as a function of the initial oligonucleotide-to-lipid ratio.

Both the size of the liposomes entrapping antisense as well as the entrapment efficiency depend on the initial antisense-to-lipid ratio. FIG. 6 shows that oligonucleotides can be efficiently entrapped at high antisense-to-lipid ratios. The entrapment efficiency is plotted as a function of the initial oligonucleotide-to-lipid ratio. The binding level at maximum entrapment is 0.16 mg oligonucleotide per mg of lipid (0.024 mol/mol). This corresponds to approximately 2250 oligonucleotide molecules per 100 nm liposome and demonstrates the high efficiency of this entrapment procedure. Entrapment efficiencies are about 3 orders of magnitude higher than obtained by passive encapsulation.

Upon increasing the oligonucleotide-to-lipid ratio, the size as well as the polydispersity of the samples increase slightly from 70±10 nm for liposomes alone to 110±30 for an initial ODN-to-lipid weight ratio of 0.2. Freeze-fracture electron microscopy showed an increase in the number of larger liposomes with increasing initial oligonucleotide-to-lipid ratios. As an aside it should be noted that the initially translucent liposome dispersion becomes increasingly turbid as the antisense-to-lipid ratio is increased.

Example 12

It would be expected that the PEG coating would inhibit formation of the closely opposed membranes observed for the multilamellar structures by TEM. The fate of PEG-Cer was therefore examined by using radioactively-labeled PEG-$CerC_{14}$. Antisense oligonucleotides were encapsulated in liposomes containing trace amounts of [$^3$H]-PEG-$CerC_{14}$ in addition to 10 mol % unlabeled PEG-$CerC_{14}$ and [$^{14}$C]-cholesterol hexadecylether (CHE) as a cholesterol marker at a [$^3$H]/[$^{14}$C] ratio of 5.9. This ratio represents an apparent PEG-Cer/chol ratio and will be used in place of the molar PEG-Cer/chol ratio. The initial antisense-to-lipid weight ratio was 0.29. Entrapment resulted in a final antisense-to-lipid ratio of 0.16. Free PEG-Cer and PEG micelles were separated from liposomes by ultracentrifugation using a sucrose step gradient (1%, 2.5%, 10%, 15% (w/v) sucrose in HBS). Empty liposomes band at the interface between 2.5% and 10% sucrose with an apparent PEG-Cer/chol ratio of 5.5. This band accounts for roughly 80% of the total lipid. The antisense-containing liposomes show a faint band at the same location, which corresponds to less than 9% of total lipid. However, most of the liposomal antisense migrates down to the 15% sucrose layer or pellets at the bottom. A complete analysis of the liposome-containing fractions of the gradient is presented in Table 9. The results are representative for samples prepared at high oligonucleotide-to-lipid ratios. It can be seen that the relative PEG-Cer/chol ratios progressively decrease towards the bottom of the gradient. More than 50% of the PEG-Cer is lost from the bottom fraction relative to the initial liposomes (apparent PEG-Cer/chol ratio 5.5). The DSPC/Chol ratio does not change. 27% of the PEG-Cer can be found in the top fractions along with 6.6% of cholesterol. Approximately the same amount of non liposome-associated PEG-Cer was found for the empty control liposomes.

Further analysis of the fractions of the above gradient show that the antisense-containing liposomes show large differences in their antisense content and size (Table 9). The oligonucleotide-to-lipid ratios as well as the average size increase from top to bottom. Three main populations can be identified as distinct bands (Table 10). Their relative proportions depended on the initial oligonucleotide-to-lipid ratio (Table 10). First, liposomes entrapping antisense at low ODN/lipid ratio (0.03–0.05). Secondly, liposomes with an ODN/lipid ratio of 0.14–0.15 and finally, liposomes with very high ODN/lipid ratios (0.29 mg/mg). The latter population decreases in favor of the first two with decreasing initial ODN/l ratio. It is optically turbid whereas the other two are translucent. It was attempted to correlate the observed differences in entrapment and size to the morphological heterogeneity seen by cryo-TEM. Antisense was entrapped at high initial oligonucleotide-to-lipid ratio (0.28 mg/mg) and the two main fractions corresponding to fractions 15 and 17 in Table 10 viewed by cryo-TEM after removal of sucrose by dialysis. The upper fraction consists exclusively of bilamellar liposomes, many of which exhibit bulbs, whereas the bottom fraction contained a mixture of bi- and multilamellar liposomes.

TABLE 9

| fraction | % PEG-Cer | % Chol | % DSPC | Chol/DSPC [mol/mol] | PEG-Cer/chol ratio [r.u.] | Size [nm] |
|---|---|---|---|---|---|---|
| b.u. | — | — | — | 2.2 | 5.9 | 86 ± 24 |
| 1–10 | 26.8 | 6.6 | — | — | — | — |
| 11 | 13.7 | 9.2 | — | — | 8.6 | 89 ± 21 |
| 12 | 4.3 | 3.9 | — | — | 6.4 | — |
| 13 | 3.6 | 4.1 | — | — | 5.0 | — |
| 14 | 8.9 | 11.4 | — | — | 4.5 | 83 ± 21 |
| 15 | 27.1 | 36.6 | 37.6 | 2.2 | 4.2 | 70 ± 15 |
| 16 | 8.5 | 12.8 | — | — | 3.8 | 75 ± 16 |
| 17 | 7.1 | 15.4 | 15.5 | 2.2 | 2.6 | 129 ± 39 |

TABLE 10

| | High initial ODN/lipid ratio | | | Low initial ODN/lipid ratio | | |
|---|---|---|---|---|---|---|
| Fraction | % lipid | % ODN | ODN/l | % lipid | % ODN | ODN/l |
| b.u. | — | — | 0.156 | — | — | 0.1 |
| 11 | 9.2 | 1.9 | 0.030 | 15.7 | 6.7 | 0.036 |
| 12 | 3.9 | 3.1 | 0.117 | 14.8 | 8.9 | 0.050 |
| 13 | 4.1 | 3.9 | 0.140 | 3.8 | 3.4 | 0.09 |
| 14 | 11.4 | 10.5 | 0.140 | 8.1 | 11.2 | 0.14 |
| 15 | 36.6 | 36.2 | 0.148 | 31.5 | 45.9 | 0.146 |
| 16 | 12.8 | 14.4 | 0.168 | 9.7 | 15.4 | 0.16 |
| 17 | 15.4 | 30.1 | 0.29 | 5.3 | 8.5 | 0.162 |

Example 13

The addition of oligonucleotides to cationic liposomes in the presence of ethanol can give rise to domain formation. The formation of the multilamellar liposomes seen must be preceded by liposome adhesion. However, 10 mol % PEG-Cer completely inhibits adhesion in the absence of ethanol. In the presence of ethanol, two effects could contribute to liposome adhesion: first, the increase in the amount of non membrane-incorporated PEG-Cer through rapid lipid exchange and second, formation of small domains depleted in PEG-Cer and enriched in antisense oligonucleotides. The latter possibility was investigated. The effect of oligonucleotide binding was visualized by phase contrast and fluorescence microscopy using giant DSPC/Chol/DODAP/PEG-CerC$_{14}$ liposomes in conjunction with FITC-labeled oligonucleotides. Most of the liposomes observed were multilamellar and displayed internal structure. In the absence of ethanol, the giant liposomes disintegrated into irregularly-shaped aggregates and smaller liposomes on addition of antisense. The green FITC fluorescence revealed the location of the oligonucleotides. A completely different picture is presented in the presence of 40% ethanol. The initially round liposomes adopt a pear-shaped form 5–10 min after addition of oligonucleotide with the oligonucleotides located in a semicircle on one side of these structures. The interior membranes are squeezed out from this horseshoe, which detaches and collapses, in particular upon raising the temperature, into a compact slightly irregular structure that appears completely green in fluorescence. The segregation of the oligonucleotides indicates that ethanol is able to stimulate domain formation.

Example 14

Figure 7:
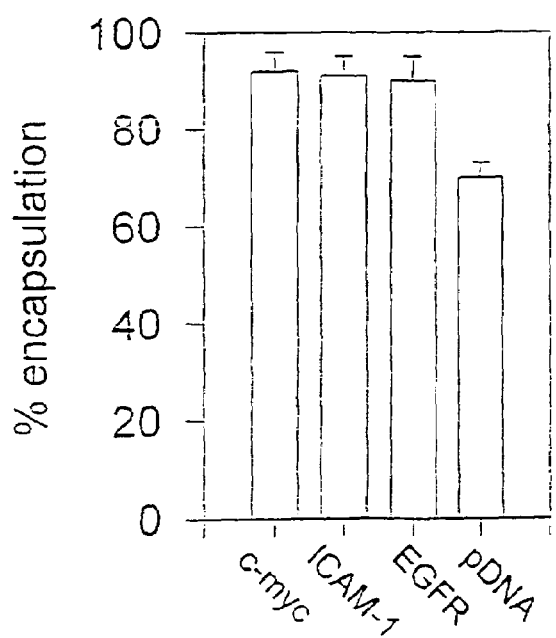
FIG. 7 shows encapsulation efficiency for several species of antisense oligodeoxynucleotides and for plasmid DNA (pDNA).

The encapsulation procedure of the invention is not dependent on a particular oligonucleotide and lipid composition, nor is it restricted to the high citrate concentrations used. Encapsulation is most efficient in 50 mM citrate buffer and decreases at higher as well as at lower citrate concentrations. The size and polydispersity increases considerably at citrate concentrations below 25 mM. FIG. 7 shows that other oligonucleotides than c-myc (Seq, ID No 1) as well as plasmid-DNA can be efficiently entrapped in DSPC/Chol/DODAP/PEG-CerC$_{14}$ liposomes. The initial oligonucleotide-to-lipid weight ratio was 0.1 mg/mg, 300 mM citrate buffer was used for oligonucleotide entrapment. The pDNA entrapment was performed in 50 mM citrate buffer at a pDNA-to-lipid weight ratio of 0.03. Unlike phosphorothioate antisense oligonucleotides phosphodiester-based molecules cannot be encapsulated high ionic strengths buffers such as 300 mM citrate buffer. This probably reflects differences in binding affinities (Semple et al., 2000). In contrast to the efficient encapsulation of large molecules, less than 10% of ATP could be entrapped in DSPC/Chol/DODAP/PEG-CerC$_{14}$ liposomes at an initial ATP-to-lipid ratio of 0.2 mg/mg. The ATP entrapment was performed in 50 mM citrate buffer. Table 5 demonstrates that the entrapment procedure can be extended to other lipid compositions including DOPE systems. Preliminary results with negatively charged liposomes and positively charged polyelectrolytes including polylysines show that entrapment is a general feature of the interaction of polyelectrolytes with oppositely charged liposomes in ethanol.

Example 15

Octylglucoside (OGP) was used in place of ethanol. The detergent was added to liposomes (1:1 v/v) to final concentrations ranging from 30–40 mM. All the subsequent steps were performed as described as in Example 5 except for the initial dialysis step against pH 4 citrate buffer, which was extended to 5 hrs. The oligonucleotide was shown to be protected from externally added OliGreen, a flourescent oligo-binding dye. The initial oligonucleotide-to-lipid ratio was 0.23 (mg/mg). Sizes represent number-averaged sizes. DSPC/Chol/DODAP/PEG-CerC$_{14}$ (20/45/25/10 mol %). The observed levels of encapsulation and final particle size are summarized in Table 11.

TABLE 11

| OGP [mM] | % encapsulation | Size [nm] |
|---|---|---|
| 30 | 51 | 65 ± 12 |
| 35 | 57 | 100 ± 22 |
| 40 | 55 | 145 ± 38 |

Using this invention, and the teachings of this specification, those skilled in the art will be able to identify other methods and means for generating fully encapsulated lipid-therapeutic agent particles, all of which are encompassed by the claims set out below.

REFERENCES

Albersdorfer, A., T., Feder, and E., Sackmann. 1997. Adhesion-induced domain formation by interplay of long-range repulsion and short-range attraction force: a model membrane study. *Biophys. J.* 73, 245–57.

Almog, S., B. J., Litman, W., Wimley, J., Cohen, E. J., Wachtel, Y., Barenholz, A., Ben-Shaul, D., Lichtenberg. 1990. States of aggregation and phase transformations in mixtures of phosphatidylcholine and octyl glucoside. *Biochemistry* 29, 4582–4592.

Angelova, M. I., N., Hristova, and I., Tsoneva. 1999. DNA-induced endocytosis upon local microinjection to giant unilamellar cationic vesicles. *Eur. Biophys. J.* 28,142–50.

Bailey, A. L., and P. R., Cullis. 1994. Modulation of membrane fusion by asymmetric transbilayer distributions of amino lipids. Biochemistry 33, 12573–80.

Barchfeld, G. L., and D. W., Deamer. 1988. Alcohol effects on lipid bilayer permeability to protons and potassium relation to action of general anesthetics. *Biochim. Biophys. Acta* 944, 40–48.

Barry, J. A., and K., Gawrisch. 1995. Direct NMR evidence for ethanol binding to the lipid-water interface of phospholipid bilayers. Biochemistry 33, 8082–88.

Bligh, E. G., and W. J., Dyer. 1959. *Can. J. Biochem. Physiol.* 37,911–17.

Bozzola, J. J., and L. D., Russell. 1999. Electron Microscopy. Chapter 19—Interpretation of micrographs. Jones and Bartlett Publishers, Toronto.

Chonn, A., and P. R., Cullis. 1998. Recent advances in liposome technologies and their applications for systemic gene delivery. *Adv. Drug Del. Rev.* 30, 73–83.

Duportail, G., and Lianos, P. (1996) Fluorescence probing of vesicles using pyrene and pyrene derivatives. In Vesicles (M. Rosoff, ed.). p. 295–366. Marcel Dekker Inc., N.Y.

Evans, E. A., and V. A., Parsegian. 1983. Energetics of membrane deformation and adhesion in cell and vesicle aggregation. *Ann. N.Y. Acad. Sci.* 416, 13–33.

Felgner, P. L., T. R., Gadek, M., Holm, R., Roman, H. S., Chan, M., Wenz, J. P., Northrop, G. M., Ringold, and H. Danielson. 1987. Lipofection: a highly efficient, lipid-mediated DNA transfection procedure. *Proc. Natl. Acad. Sci. USA* 84, 7413–17.

Felgner, P. L. 1997. Nonviral strategies for gene therapy. *Scientific American* 276, 102–106.

Fiske, C. H., and Y., Subbarow. 1925. J. Biol. Chem. 66:325–329.

Gao, X., and L., Huang. 1995. Cationic liposome-mediated gene transfer. *Gene Therapy* 2, 710–722.

Gennis, R. B. 1989. Biomembranes: Molecular Structure and Function. Springer Verlag, N.Y.

Gustafsson, J., G., Arvidson, G., Karlsson, and M., Almgren. 1995. Complexes between cationic liposomes and DNA visualized by cryo-TEM. *Biochim. Biophys. Acta* 1235, 305–12.

Hirschbein, B. L., and K. L., Fearon. 1997. P-31 NMR spectroscopy in oligonucleotide research and development—commentary. *Antisense & Nucleic Acid Drug Development* 7, 55–61.

Hoekstra, D. 1990. Fluorescence assays to monitor membrane fusion: potential application in biliary lipid secretion and vesicle interactions. Hepatology 12, 61S–66S.

Holte, L. L., and K., Gawrisch. 1997. Detecting ethanol distribution in phospholipid multilayers with MAS-NOESY Spectra. Biochemistry 36, 4669–74.

Huebner, S., B. J., Battersby, R., Grimm, and G., Cevc. 1999. Lipid-DNA complex formation: reorganization and fusion of lipid bilayers in the presence of DNA as observed by cryo-electron microscopy. *Biophys. J.* 76, 3158–3166.

Hyatt, M. A. 1981. Principles and Techniques of Electron Microscopy. Edward Arnold Publishers, London, UK.

Kachar, B., N., Fuller, and R. P., Rand. 1986. Morphological responses to calcium-induced interactions of phosphatidylserine-containing vesicles. *Biophys. J.* 50, 779–88.

Komatsu, H., and S., Okada. 1996. Ethanol-enhanced permeation of phosphaditylcholine/phosphatidylethanolamine mixed liposomal membranes due to ethanol-induced lateral phase separation. *Biochim. Biophys. Acta* 1283, 73–79.

Lasic, D. D. 1997a. Liposomes in Gene Delivery. Chapter 7, CRC Press, Boca Raton Lasic, D. D., H., Strey, M. C. A., Stuart, R., Podgornik, and P. M., Frederik. 1997b. The structure of DNA-liposome complexes. *J. Am. Chem. Soc.* 119, 832–33.

Leckband, D. E., C. A., Helm, and J., Israelachvili. 1993. Role of calcium in adhesion and fusion of bilayers. Biochemistry 32, 1127–1140.

Lentz, B. R., W., Talbot, J., Lee, and L.-X., Zheng. 1997. Transbilayer lipid redistribution accompanies poly(ethylene glycol) treatment of model membranes but is not induced by fusion. Biochemistry 36, 2076–2083.

Lobbecke, L., and G., Cevc. 1995. Effects of short-chain alcohols on the phase behavior and interdigitation of phosphatidylcholine bilayer membranes. *Biochim. Biophys. Acta* 1237, 59–69.

Lipowsky, R. 1991. The conformation of membranes. Nature 349, 475–81.

Macdonald, P. M., K. J., Crowell, C. M., Franzin, P., Mitrakos, and D. J., Semchyschyn. 1998. Polyelectrolyte-induced domains in lipid bilayer membranes: the deuterium NMR perspective. *Biochem. Cell Biol.* 76, 452–464.

Maurer, N., A., Mori, L., Palmer, M. A., Monck, K. W. C., Mok, B., Mui, Q. F., Akhong, and P. R., Cullis. 1999. Lipid-based systems for the intracellular delivery of genetic drugs. *Mol. Membr. Biol.* 16, 129–140.

McIntyre, J. C., and R. G., Sleight. 1991. Fluorescence assay for phospholipid membrane asymmetry. Biochemistry 30:11819–27.

May, S., D., Harris, and A. Ben-Shaul. 2000. The phase behavior of cationic lipid-DNA complexes. *Biophys. J.* 78, 1681–97.

Meyer, O., D. Kirpotin, K., Hong, B., Sternberg, J. W., Park, M. C., Woodle, and D., Papahadjopoulos. 1998. Cationic liposomes coated with polyethylene glycol as carriers for oligonucleotides. *J. Biol. Chem.* 273, 15621–7.

Miller, D. C., and G. P. Dahl. 1982. Early events in calcium-induced liposome fusion. *Biochim. Biophys. Acta* 689, 165–9.

Mitrakos, P., and P. M., Macdonald. 1996. DNA-induced lateral segregation of cationic amphiphiles in lipid bilayer membranes as detected via $^2$H NMR. Biochemistry 35, 16714–22.

Needham, D., and E., Evans. 1988. Structure and mechanical properties of giant lipid (DMPC) vesicle bilayers from 20° C. below to 10° C. above the liquid crystal-crystalline phase transition at 24° C. Biochemistry 27, 8261–69.

Ollivon, M., O., Eidelman, R., Blumenthal, and A., Walter. 1988. Micell-vesicle transition of egg phosphatidylcholine and octyl glucoside. Biochemistry 27, 1695–1703.

Papahadlopoulos, D., W. J., Vail, K., Jacobson, and G., Poste. 1975. Cochleate lipid cylinders: formation by fusion of unilamellar lipid vesicles. *Biochim. Biophys. Acta.* 394, 483–91.

Radler, J. O., I., Koltover, A., Jamieson, T., Salditt, and C. R., Safinya. 1998. Structure and interfacial aspects of self-assembled cationic lipid-DNA gene carrier complexes. *Langmuir* 14, 4272–83.

Rand, R. P., B., Kachar, and T. S., Reese. 1985. Dynamic morphology of calcium-induced interactions between phosphatidylserine vesicles. *Biophys. J.* 47, 483–9.

Sackmann, E. 1994. Membrane bending energy concept of vesicle- and cell-shapes and shape transitions. *FEBS Let.* 346, 3–16.

Safinya, C. R., E. B., Sirota, D., Roux, and G. S., Smith. 1989. Universality in interacting membranes: The effect of cosurfactants on the interfacial rigidity. *Phys. Rev. Lett.* 62, 1134–37.

Semple, S. C., S. K., Klimuk, T. O., Harasym, N., Dos Santos, S. M., Ansell, K. F., Wong, N., Maurer, H., Stark, P. R., Cullis, M. J., Hope, and P., Scherrer. 2000. Efficient encapsulation of antisense oligonucleotides in lipid vesicles using ionizable aminolipids: formation of novel small multilamellar vesicle structures.

Siegel, D. P., W. J, Green, and Y., Talmon. 1994. The mechanism of lamellar-to-inverted hexagonal phase transitions: a study using temperature-jump cryotransmission electron microscopy. *Biophys. J.* 66, 402–14.

Tocanne, J. F. and J., Teissie. 1990. Ionization of phospholipids and phospholipid-supported interfacial lateral diffusion of protons in membrane model systems. *Biochim. Biophys. Acta* 1031:111–142.

Wheeler, J. J., L., Palmer, M., Ossanlou, I., MacLachlan, R. W., Graham, M. J., Hope, P., Scherrer, and P. R., Cullis. 1999. Stabilized plasmid-lipid particles: construction and characterization. *Gene Therapy* 6, 271–281.

Vierl, U., L., Lobbecke, N., Nagel, and G., Cevc. 1994. Solute effects on the colloidal and phase behavior of lipid bilayer membranes: ethanol-dipalmitoylphosphatidylcholine mixtures. *Biophys. J.* 67, 1067–1079.

Xu, Y., S. W., Hui, P., Frederick, and F. C., Szoka. 1999. Physicochemical characterization and purification of cationic liposomes. *Biophys. J.* 77, 341–53.

```
                       SEQUENCE LISTING

<160> NUMBER OF SEQ ID NOS: 3

<210> SEQ ID NO 1
<211> LENGTH: 16
<212> TYPE: DNA
<213> ORGANISM: HUMAN
<220> FEATURE:
<223> OTHER INFORMATION: c-myc

<400> SEQUENCE: 1
taacgttgag gggcat                                              16

<210> SEQ ID NO 2
<211> LENGTH: 20
<212> TYPE: DNA
<213> ORGANISM: HUMAN
<220> FEATURE:
<223> OTHER INFORMATION: ICAM-1

<400> SEQUENCE: 2
gcccaagctg gcatccgtca                                          20

<210> SEQ ID NO 3
<211> LENGTH: 15
<212> TYPE: DNA
<213> ORGANISM: HUMAN
<220> FEATURE:
<223> OTHER INFORMATION: EGFR

<400> SEQUENCE: 3
ccgtggtcat gctcc                                               15
```

Siegel, D. P., and R. M., Epand. 1997. The mechanism of lamellar-to-inverted hexagonal phase transitions in phosphatidylethanolamine: implications for membrane fusion mechanisms. *Biophys. J.* 73, 3089–3111.

Slater, S. J., C., Ho, F. J., Taddeo, M. B., Kelly, and C. D., Stubbs. Contribution of hydrogen bonding to lipid—lipid interactions in membranes and the role of lipid order: effects of cholesterol, increased phospholipid unsaturation, and ethanol. *Biochemistry* 32, 3714–3721.

Slater, J. L., and Huang, C.-H. 1988. Interdigitated bilayer membranes. *Prog. Lipid Res.* 27, 325–359.

Struck, D. K., D., Hoekstra, and R. E., Pagano. 1981. Use of resonance energy transfer to monitor membrane fusion. *Biochemistry* 20, 4093–4099.

What is claimed is:

1. A method for preparing fully lipid-encapsulated therapeutic agent particles of a charged therapeutic agent comprising the steps of combining a lipid composition comprising preformed lipid vesicles, a charged therapeutic agent, and a destabilizing agent to form a mixture of preformed vesicles and therapeutic agent in a destabilizing solvent, wherein said destabilizing solvent is effective to destabilize the membrane of the preformed lipid vesicles without disrupting the vesicles, incubating the mixture for a period of time sufficient to allow the encapsulation of the therapeutic agent within the preformed lipid vesicles, and removing the destabilizing agent, wherein the preformed lipid vesicles comprise a charged lipid which has a charge which is opposite to the charge of the charged therapeutic agent and a modified lipid having a steric barrier moiety for control of aggregation, and wherein the modified lipid is present in the preformed vesicles in an amount effective to retard, but not prevent, aggregation of the preformed vesicles.

2. The method of claim 1, wherein the charged lipid in the preformed lipid vesicles comprises a cationic lipid and the therapeutic agent is an anionic therapeutic agent.

3. The method of claim 2, wherein the cationic lipid is selected from the group consisting of
dioleyl-N,N-dimethylammonium chloride ("DODAC");
N-(2,3-dioleyloxy)propyl)-N,N,N-trimethylammonium chloride ("DOTMA");
N,N-distearyl-N,N-dimethylammonium bromide ("DDAB"); N-(2,3-dioleyloxy)propyl)-N,N,N-trimethylammonium chloride ("DOTAP");
3β-(N-(N',N'-dimethylaminoethane)-carbamoyl)cholesterol ("DC-Chol");
N-(1,2-dimyristyloxyprop-3-yl)-N,N-dimethyl-N-hydroxyethyl ammonium bromide ("DMRIE");
cationic liposomes comprising DOTMA and 1,2-dioleoyl-sn-3-phosphoethanolamine ("DOPE");
cationic liposomes comprising N-(1-(2,3-dioleyloxy)propyl)-N-(2-(sperminecarboxamido)ethyl)-N,N-dimethylammonium trifluoroacetate ("DOSPA") and DOPE;
cationic lipids comprising dioctadecylamidoglycyl carboxyspermine ("DOGS") in ethanol;
N-(2,3-dioleyloxy)propyl)-N,N-dimethylammonium chloride ("DODMA") and
1,2-Dioleoyl-3-dimethylammonium-propane ("DODAP").

4. The method of claim 2, wherein the therapeutic agent is a polynucleotide.

5. The method of claim 4, wherein the cationic lipid is selected from the group consisting of
dioleyl-N,N-dimethylammonium chloride ("DODAC");
N-(2,3-dioleyloxy)propyl)-N,N,N-trimethylammonium chloride ("DOTMA");
N,N-distearyl-N,N-dimethylammonium bromide ("DDAB"); -(2,3-dioleyloxy)propyl)-N,N,N-trimethylammonium chloride ("DOTAP");
3β-(N-(N',N'-dimethylaminoethane)-carbamoyl)cholesterol ("DC-Chol");
N-(1,2-dimyristyloxyprop-3-yl)-N,N-dimethyl-N-hydroxyethyl ammonium bromide ("DMRIE");
cationic liposomes comprising DOTMA and 1,2-dioleoyl-sn-3-phosphoethanolamine ("DOPE");
cationic liposomes comprising N-(1-(2,3-dioleyloxy)propyl)-N-(2-(sperminecarboxamido)ethyl)-N,N-dimethylammonium trifluoroacetate ("DOSPA") and DOPE;
cationic lipids comprising dioctadecylamidoglycyl carboxyspermine ("DOGS") in ethanol;
N-(2,3-dioleyloxy)propyl)-N,N-dimethylammonium chloride ("DODMA") and
1,2-Dioleoyl-3-dimethylammonium-propane ("DODAP").

6. The method of claim 4, wherein the lipid composition comprises 10 to 40 mol % of the charged lipid, 25 to 40 mol % of a neutral lipid; 35 to 55 mol % of a sterol, and 2.5 to 10 mol % of the modified lipid.

7. The method of claim 2, wherein the lipid composition comprises 10 to 40 mol % of the charged lipid, 25 to 40 mol % of a neutral lipid; 35 to 55 mol % of a sterol, and 2.5 to 10 mol % of the modified lipid.

8. The method of claim 1, wherein the lipid composition comprises 10 to 40 mol % of the charged lipid, 25 to 40 mol % of a neutral lipid; 35 to 55 mol % of a sterol, and 2.5 to 10 mol % of the modified lipid.

9. The method of claim 1, wherein the destabilizing agent is ethanol.

10. The method of claim 1, wherein the ethanol is present in the destabilizing solvent at a concentration of 25–40%.

11. The method of claim 10, wherein the charged lipid comprises a cationic lipid selected from the group consisting of
dioleyl-N,N-dimethylammonium chloride ("DODAC");
N-(2,3-dioleyloxy)propyl)-N,N,N-trimethylammonium chloride ("DOTMA");
N,N-distearyl-N,N-dimethylammonium bromide ("DDAB"); -(2,3-dioleyloxy)propyl)-N,N,N-trimethylammonium chloride ("DOTAP");
3β-(N-(N',N'-dimethylaminoethane)-carbamoyl)cholesterol ("DC-Chol");
N-(1,2-dimyristyloxyprop-3-yl)-N,N-dimethyl-N-hydroxyethyl ammonium bromide ("DMRIE");
cationic liposomes comprising DOTMA and 1,2-dioleoyl-sn-3-phosphoethanolamine ("DOPE");
cationic liposomes comprising N-(1-(2,3-dioleyloxy)propyl)-N-(2-(sperminecarboxamido)ethyl)-N,N-dimethylammonium trifluoroacetate ("DOSPA") and DOPE;
cationic lipids comprising dioctadecylamidoglycyl carboxyspermine ("DOGS") in ethanol;
N-(2,3-dioleyloxy)propyl)-N,N-dimethylammonium chloride ("DODMA") and
1,2-Dioleoyl-3-dimethylammonium-propane ("DODAP").

12. The method of claim 10 wherein the destabilizing solvent further comprises 25–300 mM citrate buffer.

13. The method of claim 1, wherein the destabilizing agent is a detergent.

14. The method of claim 13, wherein the charged lipid comprises a cationic lipid selected from the group consisting of
dioleyl-N,N-dimethylammonium chloride ("DODAC");
N-(2,3-dioleyloxy)propyl)-N,N,N-trimethylammonium chloride ("DOTMA");
N,N-distearyl-N,N-dimethylammonium bromide ("DDAB"); -(2,3-dioleyloxy)propyl)-N,N,N-trimethylammonium chloride ("DOTAP");
3β-(N-(N',N'-dimethylaminoethane)-carbamoyl)cholesterol ("DC-Chol");
N-(1,2-dimyristyloxyprop-3-yl)-N,N-dimethyl-N-hydroxyethyl ammonium bromide ("DMRIE");
cationic liposomes comprising DOTMA and 1,2-dioleoyl-sn-3-phosphoethanolamine ("DOPE");
cationic liposomes comprising N-(1-(2,3-dioleyloxy)propyl)-N-(2-(sperminecarboxamido)ethyl)-N,N-dimethylammonium trifluoroacetate ("DOSPA") and DOPE;
cationic lipids comprising dioctadecylamidoglycyl carboxyspermine ("DOGS") in ethanol;
N-(2,3-dioleyloxy)propyl)-N,N-dimethylammonium chloride ("DODMA") and
1,2-Dioleoyl-3-dimethylammonium-propane ("DODAP").

15. The method of claim 13, wherein the destabilizing solvent further comprises 25–300 mM citrate buffer.

16. The method of claim 13, wherein the destabilizing solvent comprises 25–300 nM citrate buffer.

17. The method of claim 16, wherein the charged lipid comprises a cationic lipid selected from the group consisting of
dioleyl-N,N-dimethylammonium chloride ("DODAC");
N-(2,3-dioleyloxy)propyl)-N,N,N-trimethylammonium chloride ("DOTMA");
N,N-distearyl-N,N-dimethylammonium bromide ("DDAB"); -(2,3-dioleyloxy)propyl)-N,N,N-trimethylammonium chloride ("DOTAP");
3β-(N-(N',N'-dimethylaminoethane)-carbamoyl)cholesterol ("DC-Chol");
N-(1,2-dimyristyloxyprop-3-yl)-N,N-dimethyl-N-hydroxyethyl ammonium bromide ("DMRIE");
cationic liposomes comprising DOTMA and 1,2-dioleoyl-sn-3-phosphoethanolamine ("DOPE");
cationic liposomes comprising N-(1-(2,3-dioleyloxy)propyl)-N-(2-(sperminecarboxamido)ethyl)-N,N-dimethylammonium trifluoroacetate ("DOSPA") and DOPE;
cationic lipids comprising dioctadecylamidoglycyl carboxyspermine ("DOGS") in ethanol;
N-(2,3-dioleyloxy)propyl)-N,N-dimethylammonium chloride ("DODMA") and
1,2-Dioleoyl-3-dimethylammonium-propane ("DODAP").

18. The method of claim 1, wherein the mixture is incubated at a temperature of about 40° C.

19. The method of claim 1, wherein the modified lipid is PEG-CerC$_{14}$.

20. The method of claim 1, wherein the preformed lipid vesicles comprise:
a cationic lipid,
a neutral lipid selected from the group consisting of DOPE and DSPC;
the modified lipid, and
cholesterol.

* * * * *